United States Patent
Wood et al.

(10) Patent No.: US 9,797,014 B2
(45) Date of Patent: Oct. 24, 2017

(54) METHOD OF IDENTIFYING VDJ RECOMBINATION PRODUCTS

(71) Applicant: The Babraham Institute, Cambridge, Cambridgeshire (GB)

(72) Inventors: Andrew Wood, Cambridge (GB); Daniel Bolland, Cambridge (GB); Louise Matheson, Cambridge (GB); Anne Corcoran, Cambridge (GB)

(73) Assignee: The Babraham Institute, Cambridge, Cambridgeshire (GB)

( * ) Notice: Subject to any disclaimer, the term of this patent is extended or adjusted under 35 U.S.C. 154(b) by 363 days.

(21) Appl. No.: 14/382,142

(22) PCT Filed: Mar. 1, 2013

(86) PCT No.: PCT/GB2013/050516
§ 371 (c)(1),
(2) Date: Aug. 29, 2014

(87) PCT Pub. No.: WO2013/128204
PCT Pub. Date: Sep. 6, 2013

(65) Prior Publication Data
US 2015/0031042 A1    Jan. 29, 2015

(30) Foreign Application Priority Data

Mar. 2, 2012 (GB) .................................. 1203720.6
Mar. 1, 2013 (WO) ................ PCT/GB2013/050516

(51) Int. Cl.
*C12P 19/34* (2006.01)
*C12Q 1/68* (2006.01)
*C07K 16/00* (2006.01)

(52) U.S. Cl.
CPC ............ *C12Q 1/6883* (2013.01); *C07K 16/00* (2013.01); *C12Q 1/6881* (2013.01); *C12Q 2600/158* (2013.01); *C12Q 2600/16* (2013.01)

(58) Field of Classification Search
USPC ............................................... 435/6.12, 91.2
See application file for complete search history.

(56) References Cited

U.S. PATENT DOCUMENTS

2013/0196861 A1* 8/2013 Quake ................ C12Q 1/6883
506/2
2013/0296535 A1* 11/2013 Church ............... C12Q 1/6883
530/387.1

FOREIGN PATENT DOCUMENTS

WO    WO 92/12260 A1    7/1992
WO    WO 01/27329 A2    4/2001
(Continued)

OTHER PUBLICATIONS

Collins et al., "Immunoglobulin gene rearrangement, repertoire diversity, and the allergic response" Pharm. Ther., vol. 100, No. 2, pp. 157-170 (2003).
(Continued)

*Primary Examiner* — Kenneth Horlick
(74) *Attorney, Agent, or Firm* — McDermott Will & Emery LLP

(57) ABSTRACT

The invention relates to a method of identifying VDJ recombination products which comprises the use of sequence specific enrichment and specific restriction endonuclease enzymes or other DNA-shearing approaches to provide high resolution and high throughput interrogation of antigen receptor repertoires.

27 Claims, 12 Drawing Sheets

(56) References Cited

FOREIGN PATENT DOCUMENTS

| WO | WO 2004/033728 A2 | 4/2004 |
|---|---|---|
| WO | WO 2008/026927 A2 | 3/2008 |

OTHER PUBLICATIONS

Hodges et al., "Diagnostic role of tests for T cell receptor (TCR) genes", J. Clin. Pathol., vol. 56, No. 1, pp. 1-11 (2003).

International Search Report form PCT Patent Application No. PCT/GB2013/050516, 6 pages, dated Jun. 5, 2013, application now published as International Publication No. WO 2013/128204 on Sep. 6, 2013.

Langerak et al., "Molecular and flow cytometric analysis of the Vbeta repertoire for clonality assessment in mature TCRalphabeta T-cell proliferations", Blood, vol. 98, No. 1, pp. 165-173 (2001).

Mancini et al., "TCRA gene rearrangement in immature thymocytes in absence of CD3, pre-TCR, and TCR signaling" J. Immunol., vol. 167, No. 8, pp. 4485-4493 (2001).

Panzara et al., "Analysis of the T cell repertoire using the PCR and specific oligonucleotide primers", Biotechniques, vol. 12, No. 5, pp. 728-735 (1992).

Pasqual et al., "Quantitative and qualitative changes in V-J alpha rearrangements during mouse thymocytes differentiation: implication for a limited T cell receptor alpha chain repertoire", J. Exp. Med., vol. 196, No. 9, pp. 1163-1173 (2002).

Ramasamy et al., "Improved PCR method for detecting monoclonal immunoglobulin heavy chain rearrangement in B cell neoplasms", J. Clin Pathol., pp. 770-775 (1992).

Van Dongen et al., "Design and standardization of PCR primers and protocols for detection of clonal immunoglobulin and T-cell receptor gene recombinations in suspect lymphoproliferations: report of the BIOMED-2 Concerted Action BMH4-CT98-3936", Leukemia, vol. 17, No. 12, pp. 2257-2317 (2000).

Xu et al., "Diversity in the CDR3 region of $V_H$ is sufficient for most antibody specificities", Immunity, vol. 13, No. 1, pp. 37-45 (2000).

\* cited by examiner

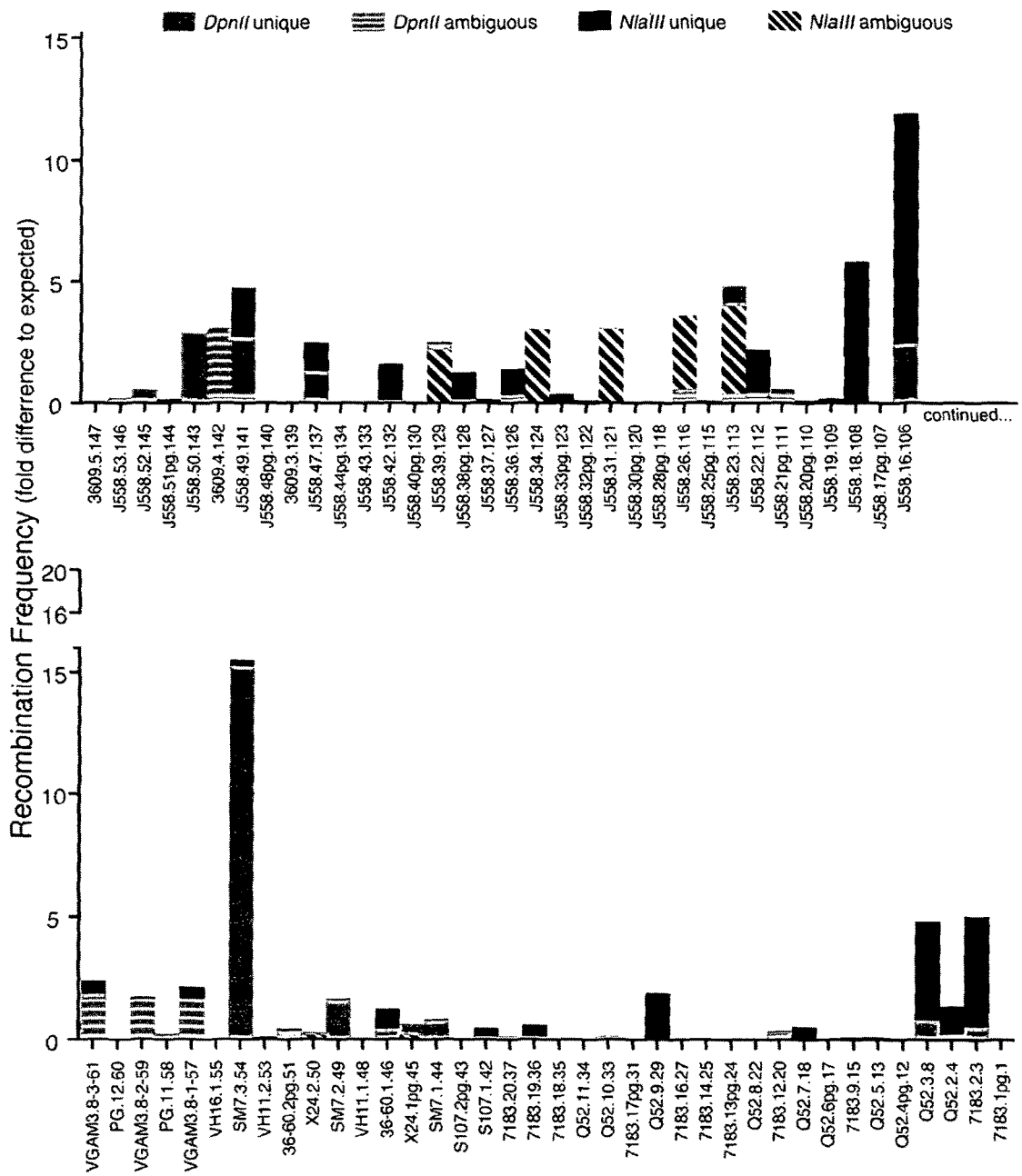
FIGURE 7 (ctd)

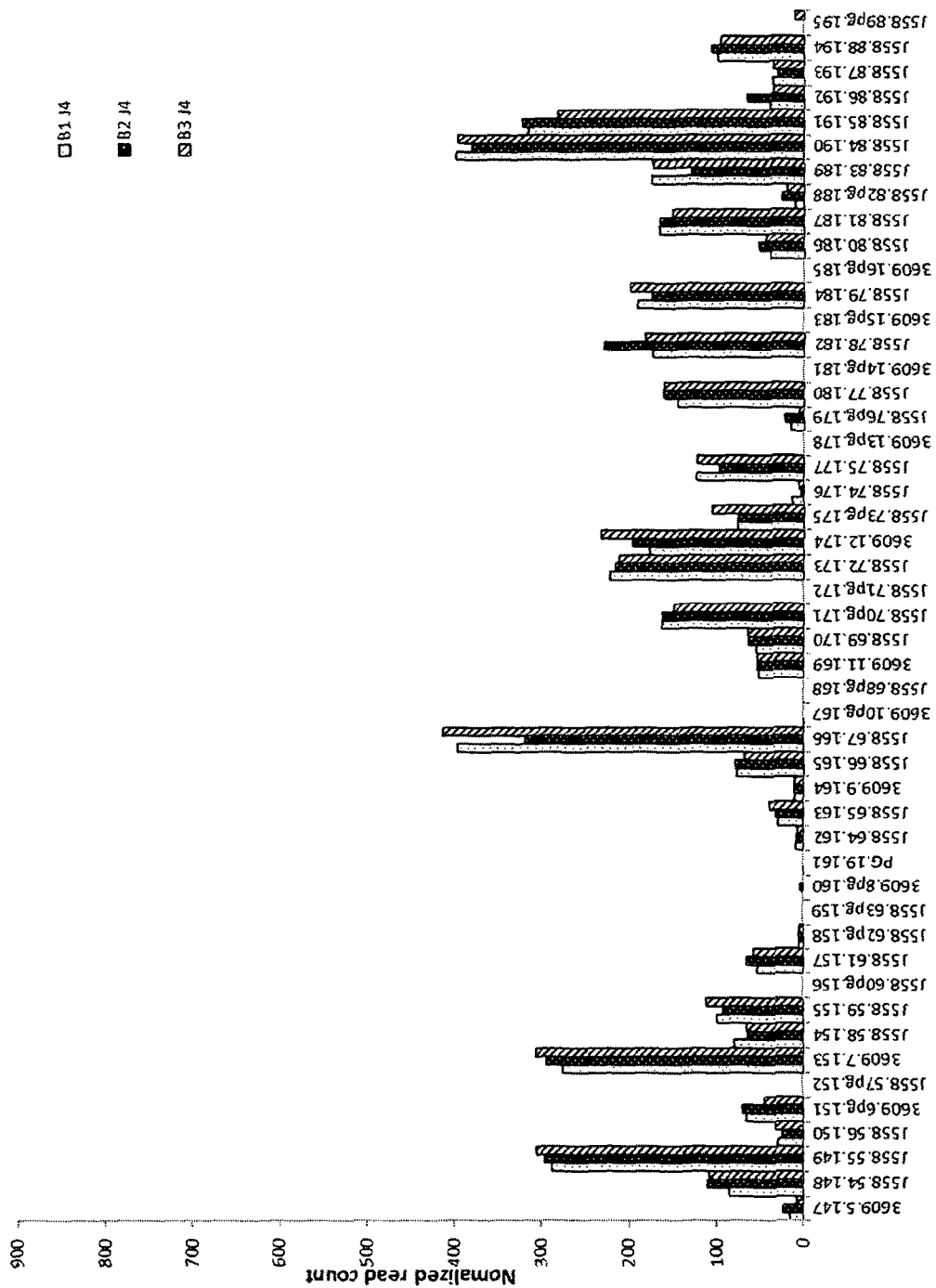

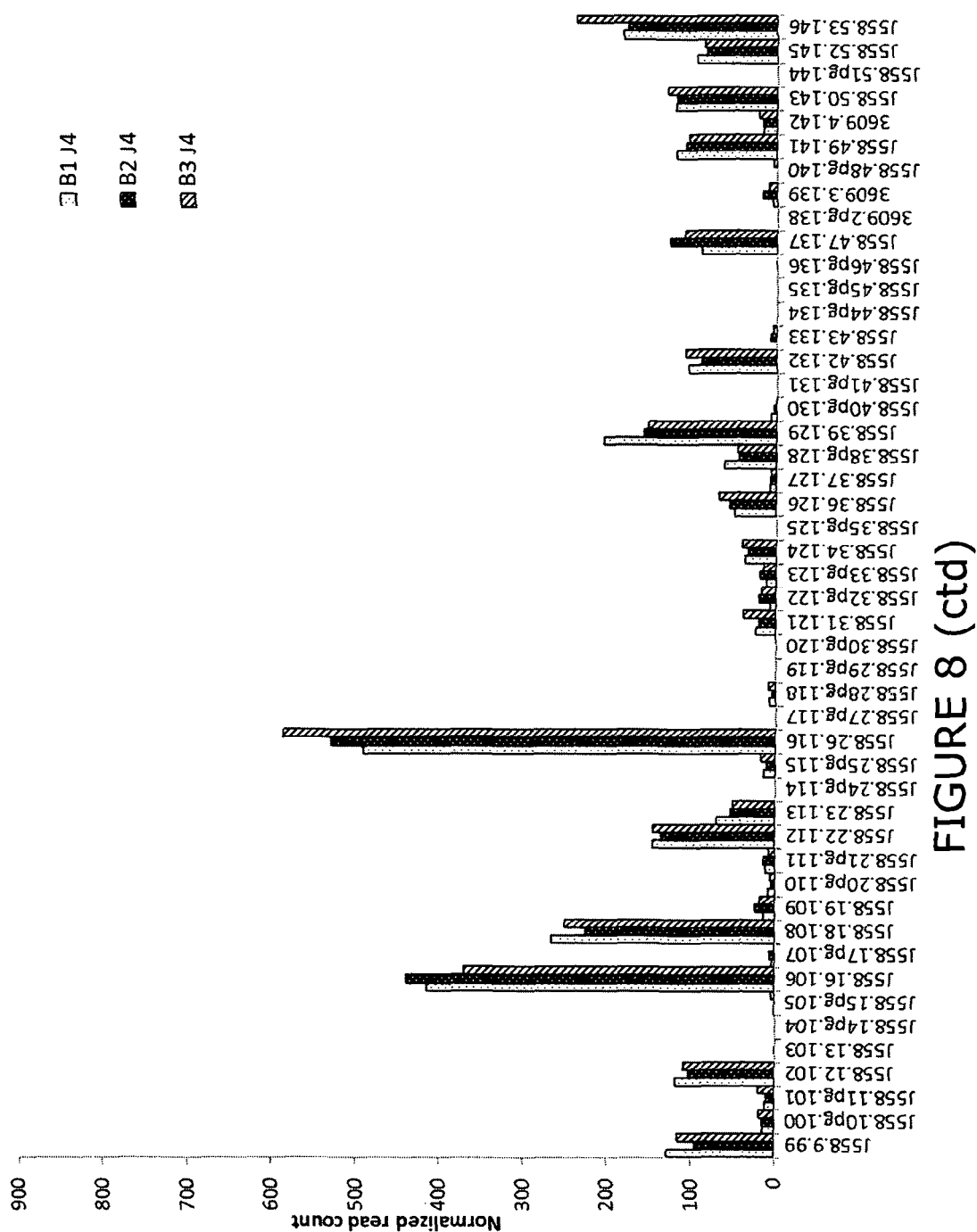
FIGURE 8 (ctd)

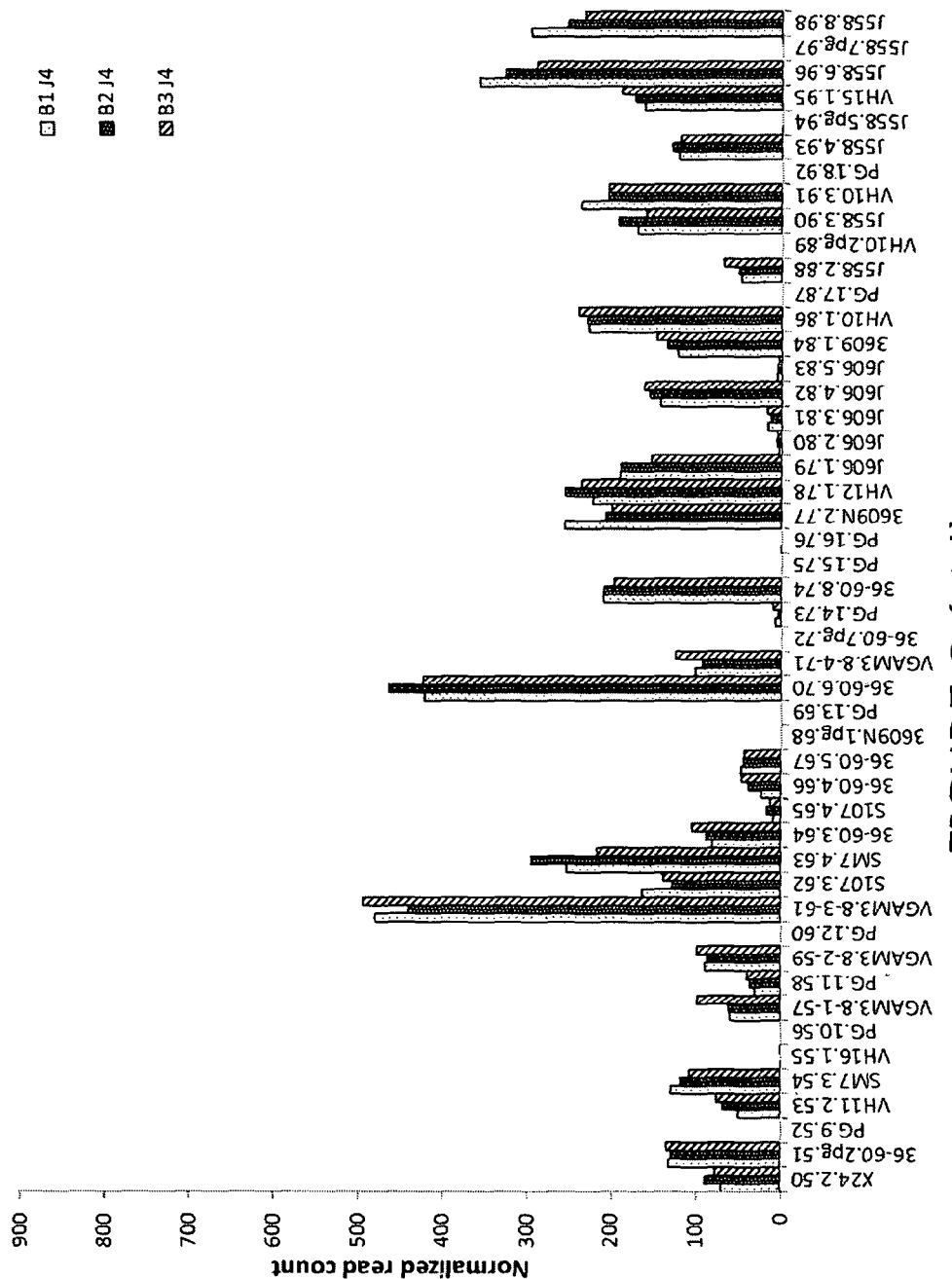
FIGURE 8 (ctd)

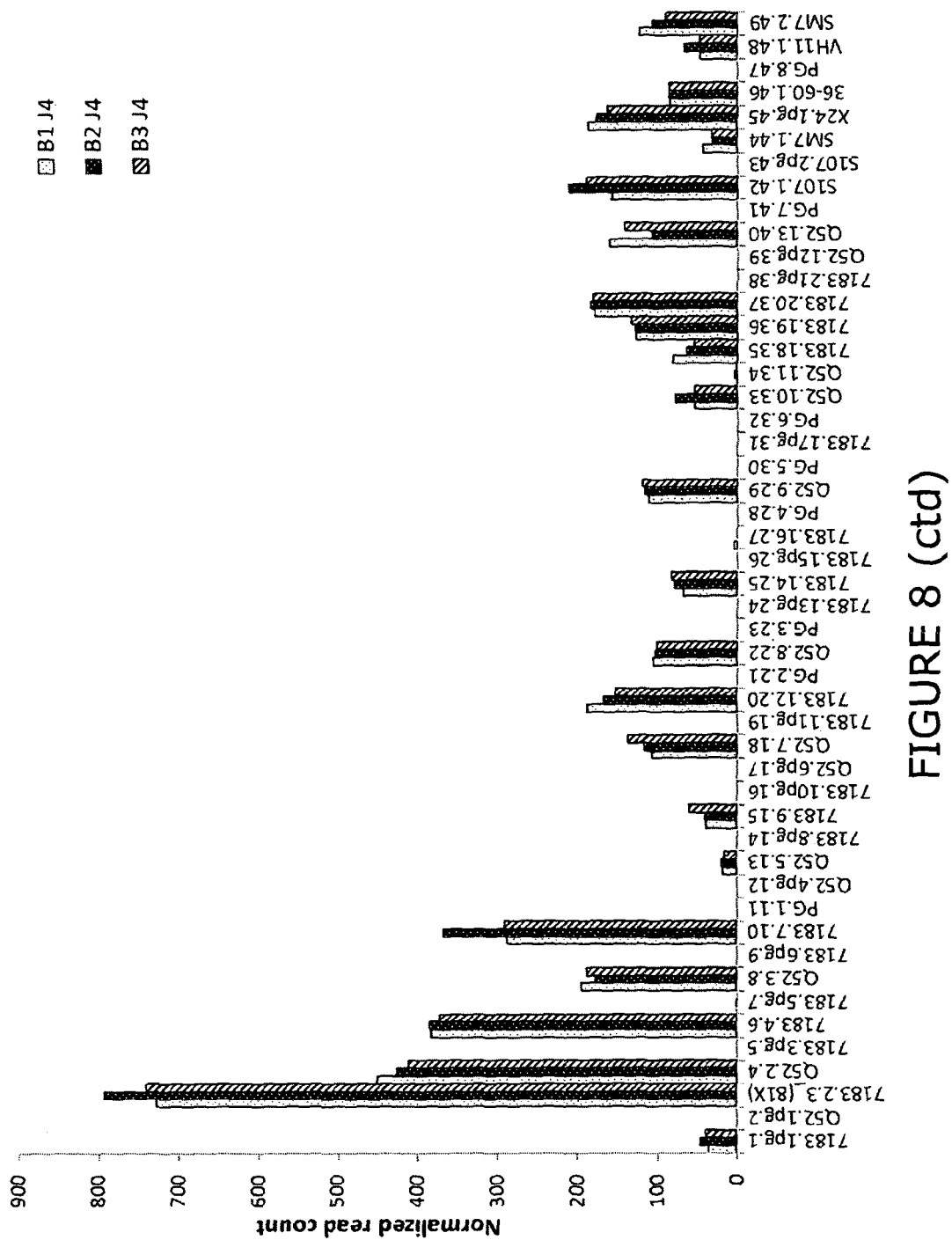
FIGURE 8 (ctd)

US 9,797,014 B2

METHOD OF IDENTIFYING VDJ RECOMBINATION PRODUCTS

CROSS-REFERENCE TO RELATED APPLICATIONS

This application is a U.S. National Stage of International Patent Application No. PCT/GB2013/050516, filed Mar. 1, 2013, which claims the benefit of priority to GB Application No. 1203720.6, filed Mar. 2, 2012, each of which is hereby incorporated by reference in its entirety.

REFERENCE TO A SEQUENCE LISTING

A Sequence Listing is submitted with this application in the form of a text file, created Aug. 20, 2014, and titled "0917430014seqlist.txt" (18,759 bytes), the contents of which are incorporated herein by reference in their entirety.

FIELD OF THE INVENTION

The invention relates to a method of identifying VDJ recombination products which comprises the use of sequence specific enrichment and specific restriction endonuclease enzymes or other DNA-shearing approaches to provide high resolution and high throughput interrogation of antigen receptor repertoires.

BACKGROUND OF THE INVENTION

VDJ recombination, also known as somatic recombination, is a mechanism of genetic recombination in the early stages of immunoglobulin (Ig) and T cell receptor (TCR) production of the immune system. VDJ recombination nearly-randomly combines Variable (V), Diverse (D) and Joining (J) gene segments of vertebrates, and because of its randomness in choosing different genes, is able to diversely encode proteins to match antigens from bacteria, viruses, parasites, dysfunctional cells such as tumor cells and pollens.

VDJ recombination of the mouse immunoglobulin heavy chain locus is pictorially shown in FIG. 1. This is a large 3 Mb locus consisting of approximately 195 variable (V) genes, 10 diversity (D) genes and 4 joining (J) genes. These are the segments that participate in VDJ recombination. There are also 8 constant genes which, as their name suggests, do not undergo VDJ recombination. The first event in the VDJ recombination of this locus is that one of the D genes rearranges to one of the J genes. Following this, one of the V genes is appended to this DJ rearrangement to form the functional VDJ rearranged gene that then codes for the variable segment of the heavy chain protein. Both of these steps is catalysed by recombinase enzymes called Rags which delete out the intervening DNA. An analogous arrangement exists in the human genome, which instead comprises 95 variable (V) genes, 20 diversity (D) genes and 6 joining (J) genes.

This recombination process takes place in a stepwise fashion in progenitor B cells to produce the diversity required for the antibody repertoire but there is another requirement—that of specificity such that each B cell only produces one antibody. This specificity is fundamental for the function of the immune system and is achieved by a process called allelic exclusion such that functional rearrangement of one allele signals via a currently unclear mechanism to prevent further recombination of the second allele.

The existing methodology uses PCR-based approaches to identify VDJ recombination products. This comprises pairs of primers, where one primer binds to one of the four J genes, common to all VDJ recombination products, or a sequence immediately downstream of a J gene, in combination with a primer or primers specific for the V gene component of the VDJ recombination product.

There are a number of weaknesses with the existing methodology. For example, there are numerous V gene families (16 in the mouse Igh), and to ensure specificity of detection, different V gene primers must be designed for each family. This introduces a bias in quantitative comparative analysis, since amplification of individual V gene families will depend on the relative efficiencies of the V gene primers designed for different V gene families, and differences in efficiency introduce inaccuracies in comparative analysis.

Even within V gene families, the V gene members have slightly different sequences and thus, unless a primer can be designed that matches each V gene member sequence 100%, this will introduce bias in comparative amplification of V genes within a family. For larger V gene families, and thus the majority of V genes, it is virtually impossible to design a V gene primer that can detect all V family members. The only way to circumvent this is to design primers to subsets of V genes within a family, but this introduces an additional bias again, due to different efficiency of amplification with different PCR primers. The combination of these two problems means that current methods cannot provide an unbiased and complete analysis of the VDJ recombination products in a sample.

The current PCR-based methods also have a problem with scale. The usual step after PCR amplification is to clone and sequence the PCR products. As an example, there are almost 200 V genes in the mouse Igh. The most frequent aim is to determine how often these are used relative to each other in the immunoglobulin repertoire. In order to detect each different V gene once, assuming they were recombined at equal efficiency and detected by PCR with equal efficiency (neither of which is the case), 200 clones would have to be sequenced. To actually determine relative usages of V genes in a population in which they are used at frequencies that can differ by orders of magnitude, tens of thousands of clones would have to be generated and sequenced. This is currently prohibitive, both in terms of cost and labour.

Some attempts have been made to overcome the problem of scale by incorporating next generation sequencing approaches into the methodology. Although several of these have been described recently, they all continue to use PCR primers for the V gene families as the starting point for detection of VDJ recombination products, and subsequently incorporate next generation sequencing as a method of 'cloning and sequencing' large numbers of PCR products. Thus the inherent biases due to PCR primer efficiency remain.

There is therefore a great need to provide improved methods of identifying VDJ recombination products which overcome one or more of the aforementioned problems.

SUMMARY OF THE INVENTION

According to a first aspect of the invention, there is provided a method of identifying a VDJ recombination product which comprises the following steps:

(a) obtaining a nucleic acid sample comprising a VDJ recombination product;

(b) when said nucleic acid sample comprises DNA, fragmenting the VDJ recombination product either by sonication, shearing or performing a restriction endonuclease reaction at a first site downstream of each of the J genes or downstream of the constant region, and a second site within or immediately upstream of the V gene to generate digested VDJ recombined fragments and unrecombined J fragments;

(c) when said nucleic acid sample comprises DNA, annealing oligonucleotides to the digested fragments at unique regions within or immediately downstream of each of the J genes, and when the nucleic acid sample is cDNA or RNA, annealing oligonucleotides to the VDJ recombination product at a position specific to the constant region or J gene;

(d) when said nucleic acid sample comprises DNA, separating the digested VDJ recombined fragments from the unrecombined J fragments and the rest of the genome;

(e) sequencing the VDJ recombined fragments or products; and (f) data processing of the sequencing data to identify each VDJ recombination product and quantify VDJ recombination frequencies.

According to a further aspect of the invention, there is provided a kit for identifying VDJ recombination products which comprises instructions to use said kit in accordance with the methods described herein.

According to a further aspect of the invention, there is provided a VDJ recombination product obtainable by the method as described herein.

According to a further aspect of the invention, there is provided a VDJ recombination product or a method of identifying a VDJ recombination product as described herein for use in monitoring an immunodeficiency disorder.

BRIEF DESCRIPTION OF THE FIGURES

FIG. 8 provides a detailed picture of the recombination frequency for Example 2 with sonication in Mouse proB cells and Igh; B1, B2, B3 are replicate samples; J4 indicates VDJ recombined sequences including J4.

DETAILED DESCRIPTION OF THE INVENTION

Figure 1:
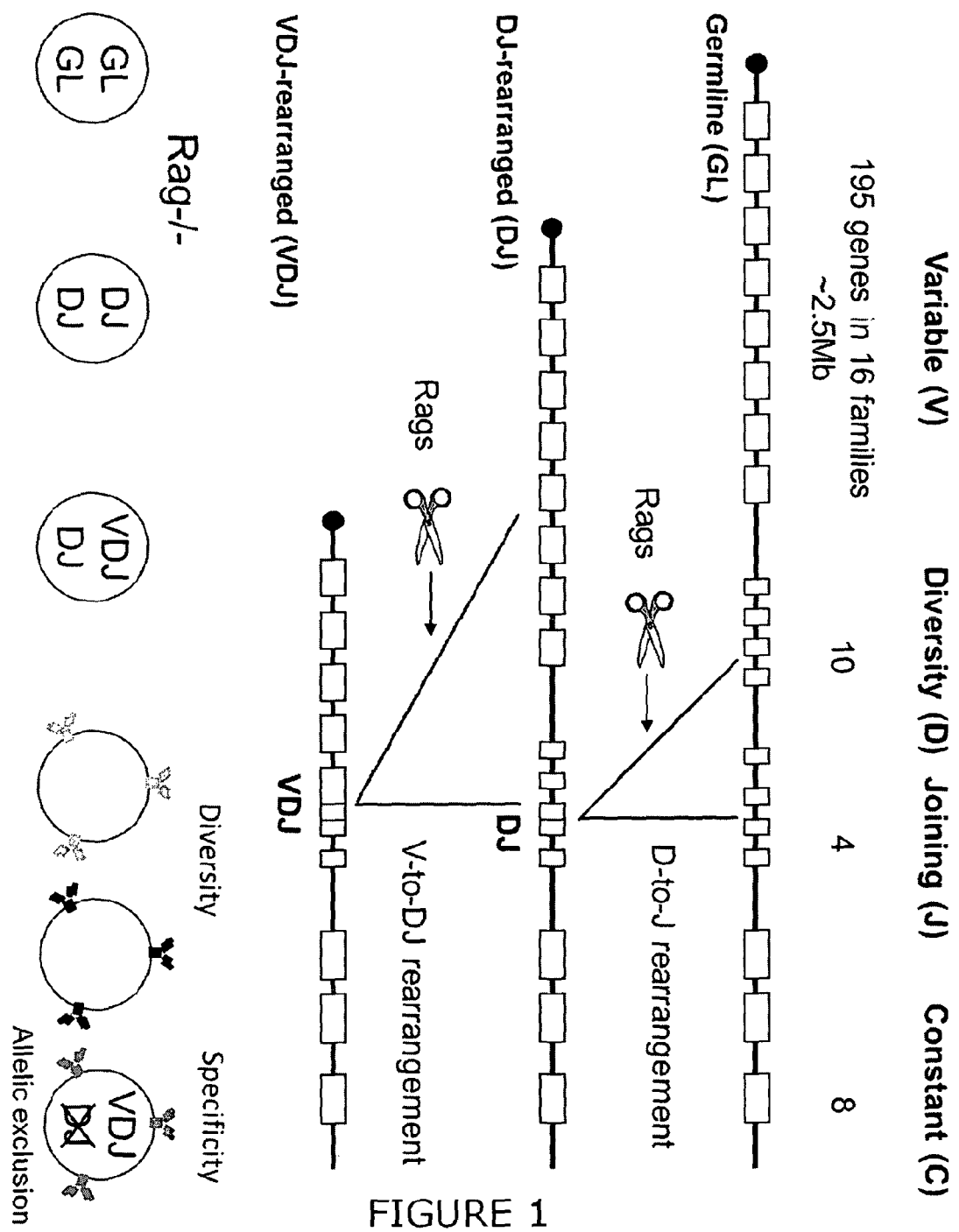
FIGS. 1 and 2 provide an overview of the concept of VDJ recombination for the generation of antibody diversity.
Figure 2:
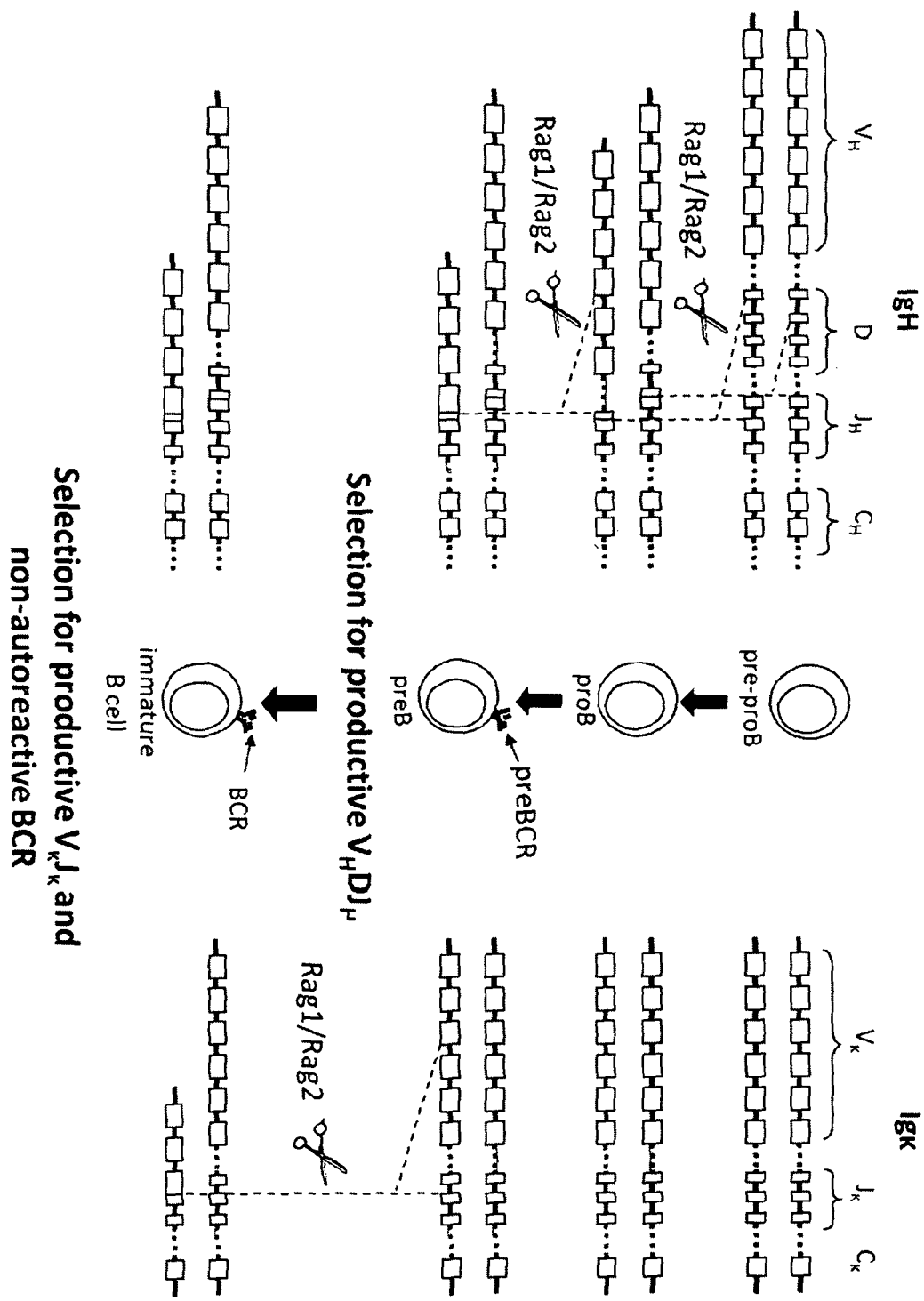
Figure 3:
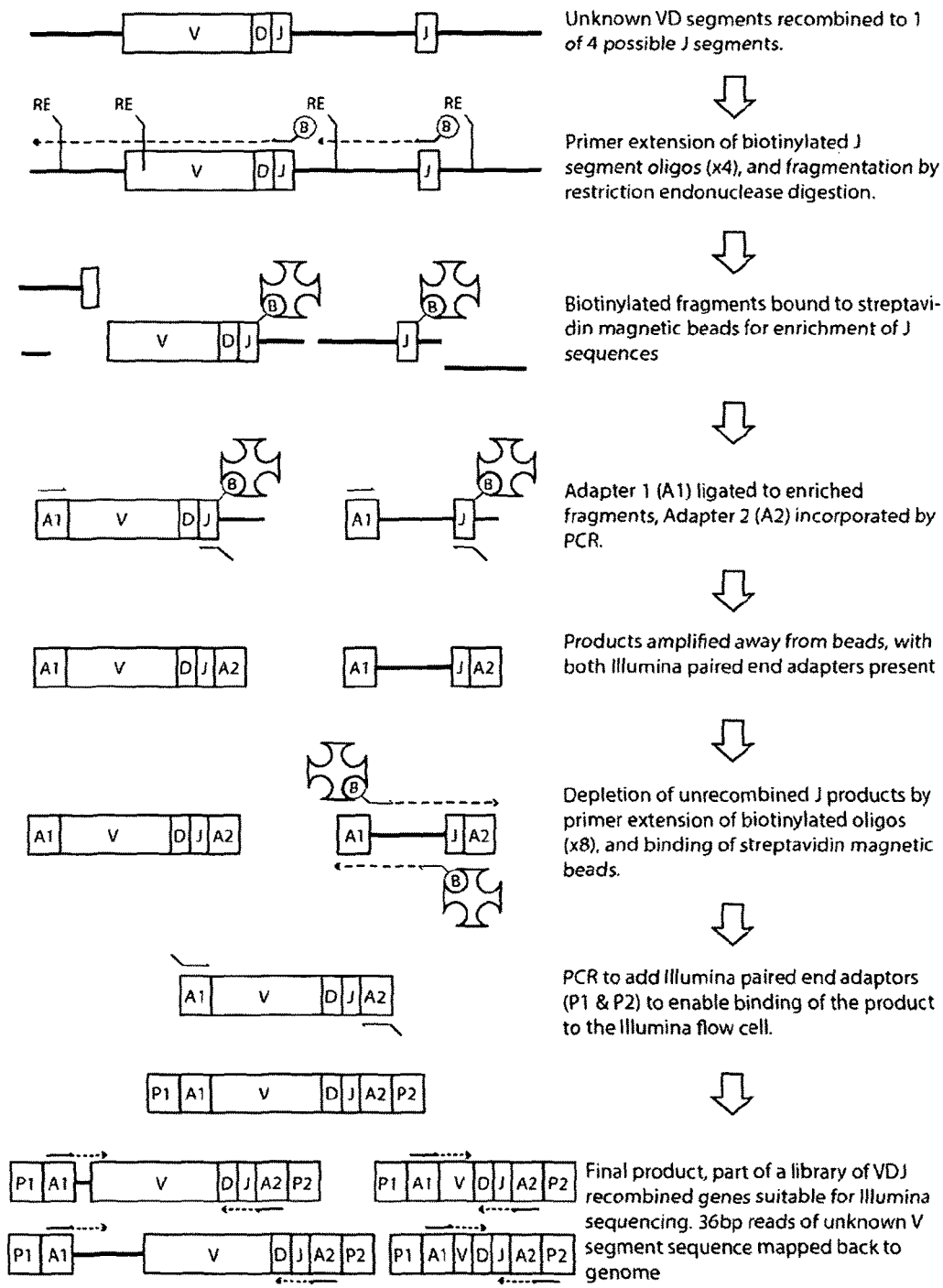
FIGS. 3-5 provide schematic overviews of alternative embodiments of the method of the invention.
Figure 4:
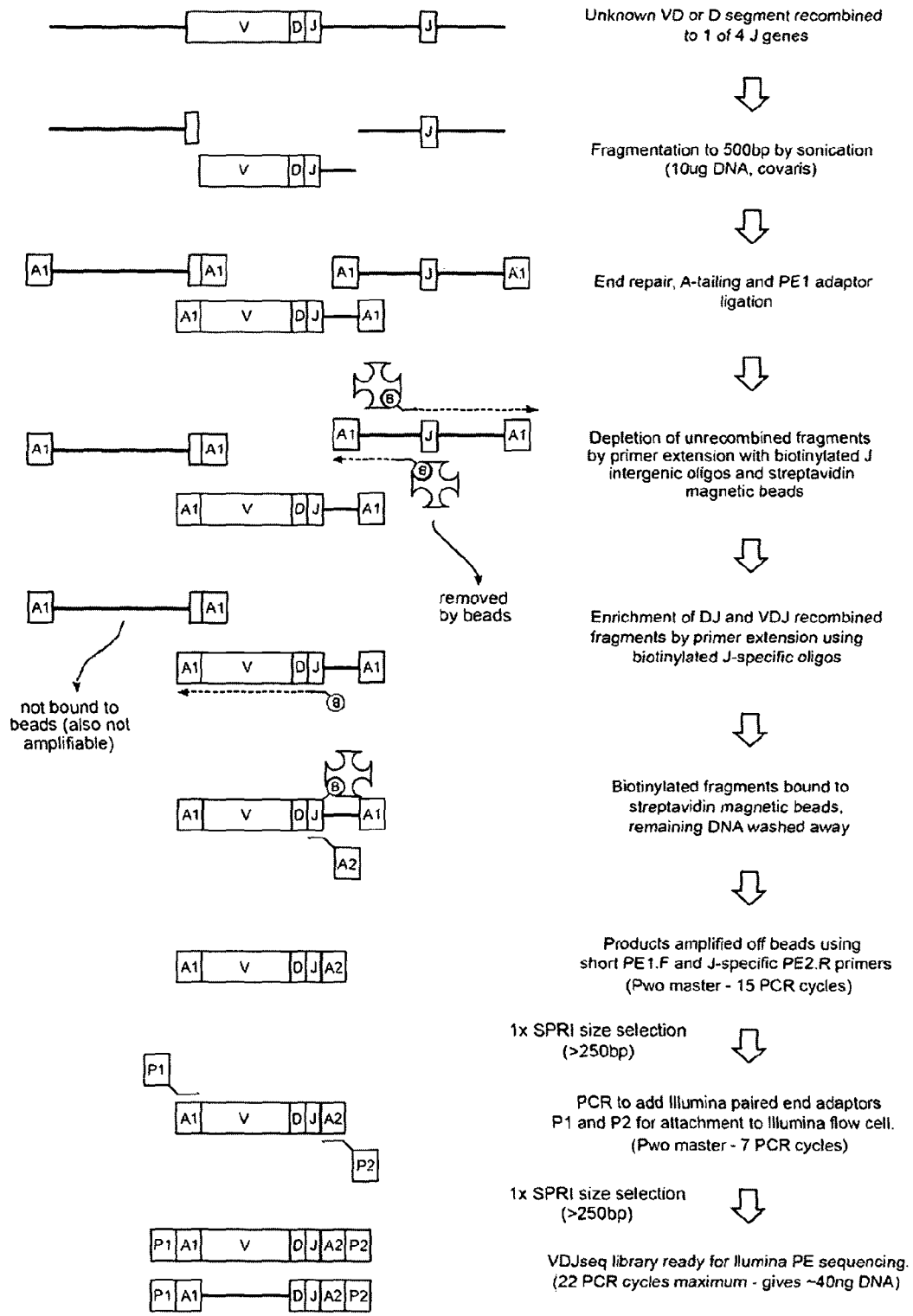
Figure 5:
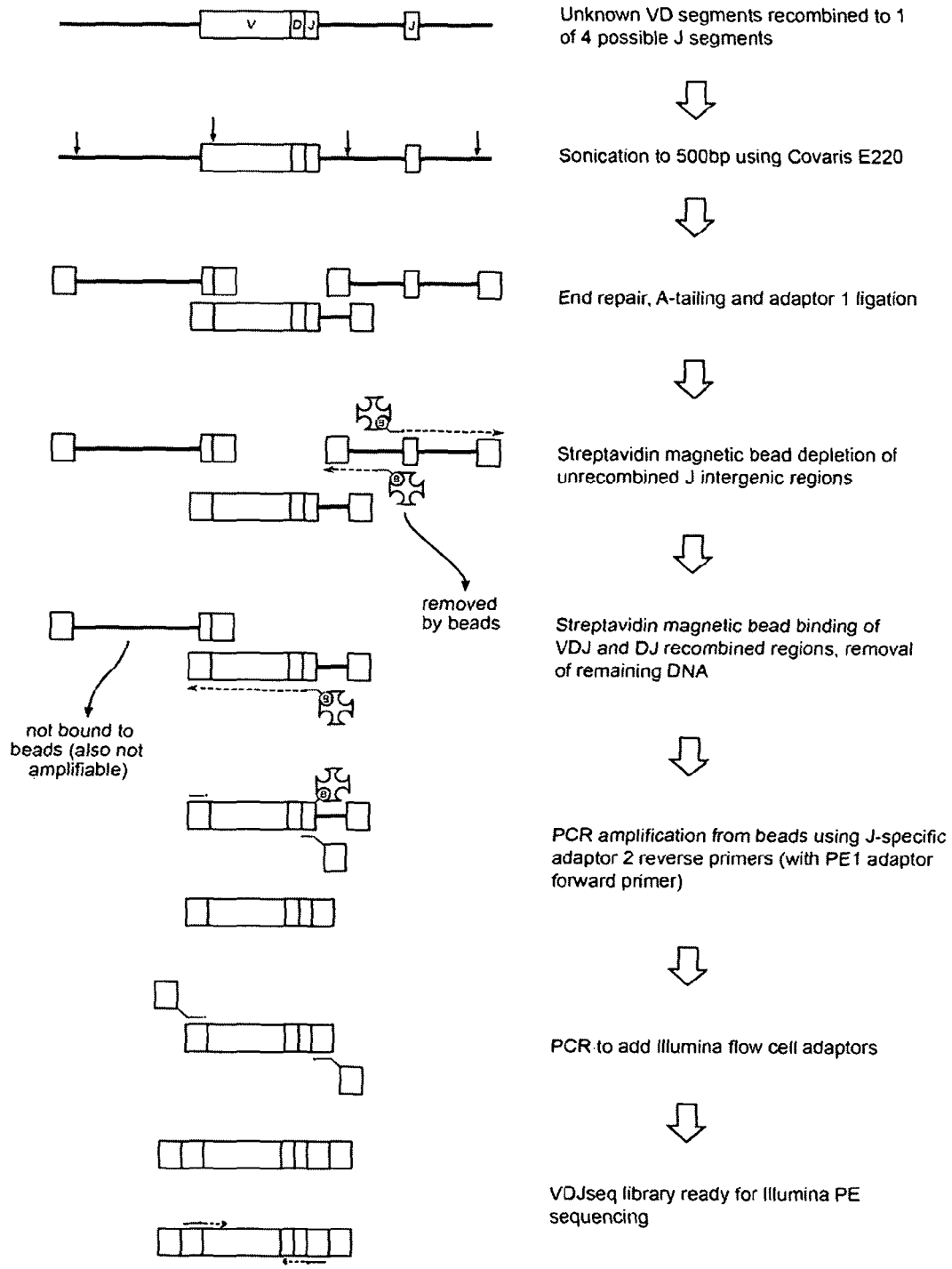
Figure 6:
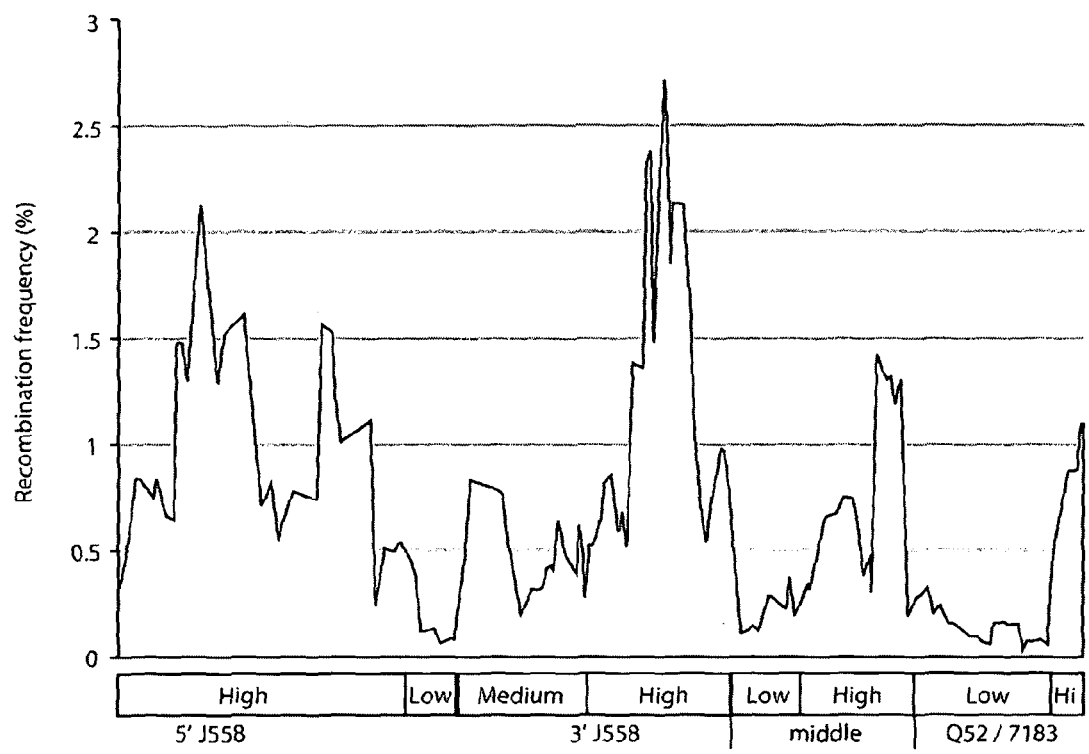
FIG. 6 provides a schematic demonstrating the high resolution comparative frequency of recombination of V genes throughout the mouse Igh V region.

According to a first aspect of the invention, there is provided a method of identifying a VDJ recombination product which comprises the following steps:

(a) obtaining a nucleic acid sample comprising a VDJ recombination product;

(b) when said nucleic acid sample comprises DNA, fragmenting the VDJ recombination product either by sonication, shearing or performing a restriction endonuclease reaction at a first site downstream of each of the J genes or downstream of the constant region, and a second site within or immediately upstream of the V gene to generate digested VDJ recombined fragments and unrecombined J fragments;

(c) when said nucleic acid sample comprises DNA, annealing oligonucleotides to the digested fragments at unique regions within or immediately downstream of each of the J genes, and when the nucleic acid sample is cDNA or RNA, annealing oligonucleotides to the VDJ recombination product at a position specific to the constant region or J gene;

(d) when said nucleic acid sample comprises DNA, separating the digested VDJ recombined fragments from the unrecombined J fragments and the rest of the genome;

(e) sequencing the VDJ recombined fragments or products; and (f) data processing of the sequencing data to identify each VDJ recombination product and quantify VDJ recombination frequencies.

According to a second aspect of the invention, there is provided a method of identifying a VDJ recombination product which comprises the following steps:

(a) obtaining a nucleic acid sample comprising a VDJ recombination product;

(b) annealing a primer specific for a unique region within or immediately downstream of each of the J genes if the nucleic acid is a DNA sample or a primer specific for the constant region if the nucleic acid is a cDNA sample;

(c) performing a primer extension reaction upon the primer annealed in step (b);

(d) fragmenting the DNA either by sonication or shearing or performing a restriction endonuclease reaction at a first site downstream of each of the J genes or downstream of the constant region primer and a second site within or immediately upstream of the V gene to generate recombined VDJ digested fragments and unrecombined J fragments;

(e) separating the recombined VDJ digested fragments from the unrecombined J fragments and the rest of the genome;

(f) sequencing the recombined VDJ digested fragments; and (g) data processing of the sequencing data to identify each VDJ recombination product and quantify VDJ recombination frequencies.

The identification method of the invention provides a number of significant advantages over conventional techniques employed to determine the nature of a repertoire. For example, the method of the invention offers a high resolution, high throughput interrogation of antigen receptor repertoires.

It will be appreciated that the invention finds great utility in the interrogation of antigen receptor repertoires in mouse immunoglobulin heavy chain IgH and Igκ and human heavy chain IgH, as described in the experimental procedure and data presented herein. However, the method has applicability to other repertoires and is also adaptable for other antigen receptor repertoires and other species, such as human, rabbit, rat and the like. The invention provides enrichment of VDJ and DJ recombined sequences along with the generation of large unbiased libraries of recombined sequences. The method of the invention allows the unambiguous identification of individual recombination events and complete details of V, D, J gene usage, N nucleotide addition and the like. The invention also has surprisingly high resolution and in particular has been able to identify a previously unknown recombination mechanism and chromosomal translocations. More particularly, the method of the invention offers advantages with respect to scalability. The method may be performed in a high throughput manner and as shown in the Examples described herein, approximately 100,000 unique VDJ recombinations were captured and identified which represents a 1000 fold increase over existing methods.

In one embodiment, the nucleic acid sample comprising a VDJ recombination product comprises a cell population. It will be appreciated that the cell population may be obtained from any species or organism containing transgenic antigen receptor loci. In one embodiment, the cell population is obtained from a mouse, such as a transgenic mouse. In an alternative embodiment, the cell population is obtained from a human.

It will be appreciated that the cell population will comprise any suitable population of cells which would contain a VDJ recombination product. In one embodiment, the cell population comprises an immunoglobulin containing cell. In a further embodiment, the immunoglobulin containing cell comprises a white blood cell. In a yet further embodiment, the white blood cell comprises a lymphocyte, such as a small lymphocyte. In a yet further embodiment, the small lymphocyte comprises a T cell or a B cell, such as a B cell.

In one embodiment, the VDJ recombination product is derived from a heavy chain immunoglobulin. In the developing B cell, the first recombination event to occur is between one D and one J gene segment of the heavy chain locus. Any DNA between these two genes is deleted. This D-J recombination is followed by the joining of one V gene, from a region upstream of the newly formed DJ complex, forming a rearranged VDJ gene. All other genes between V and D segments of the new VDJ gene are now deleted from the cell's genome. Primary transcript (unspliced RNA) is generated containing the VDJ region of the heavy chain and both the constant mu and delta chains ($C_\mu$ and $C_\delta$). (i.e. the primary transcript contains the segments: V-D-J-$C_\mu$-$C_\delta$). The primary RNA is processed to add a polyadenylated (poly-A) tail after the $C_\mu$ chain and to remove the sequence between the VDJ segment and this constant gene segment. Translation of this mRNA leads to the production of the Ig μ heavy chain protein.

In an alternative embodiment, the VDJ recombination product is derived from a light chain immunoglobulin. The kappa (κ) and lambda (λ) chains of the immunoglobulin light chain loci rearrange in a very similar manner to the heavy chain locus, except the light chains lack a D segment. For example, the first step of recombination for the light chains involves the joining of the V and J chains to give a VJ complex before the addition of the constant chain gene during primary transcription. Translation of the spliced mRNA for either the kappa or lambda chains results in formation of the Ig κ or Ig λ light chain protein. Assembly of the Ig μ heavy chain and one of the light chains results in the formation of membrane bound form of the immunoglobulin IgM that is expressed on the surface of the immature B cell.

In an alternative embodiment, the cell population comprises a T cell. In one embodiment, the VDJ recombination product is derived from a T cell receptor. During thymocyte development, the T cell receptor (TCR) chains undergo essentially the same sequence of ordered recombination events as that described for immunoglobulins. D-to-J recombination occurs first in the β chain of the TCR. This process can involve either the joining of the $D_\beta 1$ gene segment to one of six $J_\beta 1$ segments or the joining of the $D_\beta 2$ gene segment to one of seven $J_\beta 2$ segments. DJ recombination is followed (as described above) with $V_\beta$-to-$D_\beta J_\beta$ rearrangements. All genes between the $V_\beta$-$D_\beta$-$J_\beta$ genes in the newly formed complex are deleted and the primary transcript is synthesized that incorporates the constant domain gene ($V_\beta$-$D_\beta$-$J_\beta$-$C_\beta$). mRNA transcription splices out any intervening sequence and allows translation of the full length protein for the TCR $C_\beta$ chain.

The rearrangement of the alpha (α) chain of the TCR follows β chain rearrangement, and resembles V-to-J rearrangement described for Ig light chains (as described above). The assembly of the β- and α-chains results in formation of the αβ-TCR that is expressed on a majority of T cells.

T cell receptor (TCR) chains may also comprise gamma (γ) and delta (δ) chains which assemble to form γδ-TCR.

In an alternative embodiment, the nucleic acid sample comprising a VDJ recombination product comprises a library of VDJ recombined nucleic acids obtained from an in vitro antibody production system, such as ribosome display.

References herein to the term "identifying" refer to any step which enables one member of a repertoire of antigens to be differentially identified from that of another member of a repertoire of antigens.

References herein to the term "VDJ recombination product" refer to the product of a recombination event between a variable (V), diversity (D) and joining (J) gene.

In one embodiment, the nucleic acid comprises DNA or RNA obtained from the sample. In a further embodiment, the nucleic acid comprises cDNA or mRNA. In a yet further embodiment, the nucleic acid comprises cDNA. When the sample comprises a cell population, it will be appreciated that the process of obtaining nucleic acid from the cell population is readily apparent to the skilled person in accordance with standard molecular biology techniques.

In one embodiment, the nucleic acid sample is DNA. Thus, according to a further aspect of the invention, there is provided a method of identifying a VDJ recombination product which comprises the following steps:

(a) obtaining a DNA sample comprising a VDJ recombination product;

(b) fragmenting the VDJ recombination product either by sonication, shearing or performing a restriction endonuclease reaction at a first site downstream of each of the J genes or downstream of the constant region, and a second site within or immediately upstream of the V gene to generate digested VDJ recombined fragments and unrecombined J fragments;

(c) annealing oligonucleotides to the digested fragments at unique regions within or immediately downstream of each of the J genes;

(d) separating the digested VDJ recombined fragments from the unrecombined J fragments and the rest of the genome;

(e) sequencing the VDJ recombined fragments; and (f) data processing of the sequencing data to identify each VDJ recombination product and quantify VDJ recombination frequencies.

It will be appreciated that when the nucleic acid sample comprises cDNA or RNA (i.e. mRNA), steps (b) and (d) of the first aspect of the invention may be omitted. Thus, according to a further aspect of the invention, there is provided a method of identifying a VDJ recombination product which comprises the following steps:

(a) obtaining a cDNA or RNA sample comprising a VDJ recombination product;

(c) annealing oligonucleotides to the VDJ recombination product at a position specific to the constant region or J gene;

(e) sequencing the VDJ recombined products; and
(f) data processing of the sequencing data to identify each VDJ recombination product and quantify VDJ recombination frequencies.

In one embodiment of the first aspect of the invention, the oligonucleotide (e.g. a primer or in vitro transcribed RNA) used in step (c) is specific for a unique region within each of the J genes. In an alternative embodiment, the oligonucleotide used in step (c) is specific for a region immediately downstream of each of the J genes. It is beneficial for the oligonucleotide to be either within or very close to the J segment to prevent an excessive amount of bases being present when the final product is sequenced.

In one embodiment of the second aspect of the invention, the primer used in step (b) is specific for a unique region within each of the J genes. In an alternative embodiment, the primer used in step (b) is specific for a region immediately downstream of each of the J genes. It is beneficial for the primer to be either within or very close to the J segment to prevent an excessive amount of bases being present when the final product is sequenced.

It will be understood that references herein to the term "unique" refer to a sequence which is not present within the remainder of the genome. This arrangement prevents other sequences being incorrectly identified by the method of the invention.

It will be appreciated that when the cell population comprises human cells, 6 different primers will be required for each of the 6 different human J genes. In the embodiment where the cell population comprises human cells, the primers are selected from any of the primers described in SEQ ID NOS: 51 to 56. In an alternative embodiment where the cell population comprises human cells, the 6 primers may be selected from other sequences within the six human J genes.

It will also be appreciated that when the cell population comprises mouse cells, 4 different primers will be required for each of the 4 different mouse J genes. In the embodiment where the cell population comprises mouse cells, the 4 primers may be selected from any of the primers described in SEQ ID NOS: 1 to 4. In an additional embodiment where the cell population comprises mouse cells, the 4 primers may be selected from any of the primers described in SEQ ID NOS: 47 to 50. In a further embodiment, where the cell population comprises mouse cells, the 4 primers may be selected from any of the primers described in SEQ ID NOS: 1 to 4. In an alternative embodiment where the cell population comprises mouse cells, the 4 primers may be selected from other sequences within the four mouse J genes.

In an alternative embodiment, when cDNA is used as a sample nucleic acid material, a single primer is used (e.g. in step (c) of the first aspect or in step (b) of the second aspect of the invention) which is specific for a region within an exon (i.e. any specific exon) of the constant region and thus all successfully VDJ recombined (and transcribed) products are captured regardless of J gene usage.

In a further alternative embodiment, when cDNA is used as a sample nucleic acid material, a single primer is used (e.g. in step (c) of the first aspect or in step (b) of the second aspect of the invention) which is specific for a region within the first exon of the constant region and thus all successfully VDJ recombined (and transcribed) products are captured regardless of J gene usage.

In one embodiment, step (c) of the first aspect of the invention comprises tagging the digested fragments with one member of a binding pair. In a particular embodiment when primers are used, the primer additionally comprises one member of a binding pair. This embodiment provides the advantage of allowing enrichment of the target J sequences over other sequences. Examples of suitable binding pairs include biotin and streptavidin or an antigen and an antibody. In one embodiment, the tag or primer additionally comprises biotin or streptavidin, such as biotin. It will be appreciated that enrichment of a biotinylated fragment will require a streptavidin containing moiety, such as a magnetic bead containing streptavidin, for example Dynabeads from the kilobaseBINDER kit (Invitrogen).

In one embodiment, step (c) of the first aspect of the invention additionally comprises the step of performing primer extension, oligonucleotide hybridization and/or reverse transcription.

It will be appreciated that the primer extension, oligonucleotide hybridization and reverse transcription techniques required in step (c) of the first aspect of the invention are readily apparent to the skilled person in accordance with standard molecular biology techniques.

In one embodiment, the nucleic acid sample is fragmented by sonication.

In an alternative embodiment, the nucleic acid sample is fragmented by performing a restriction endonuclease reaction.

In one embodiment, the restriction endonuclease enzyme is selected from DpnII and/or NlaIII.

In a particular embodiment, where the cell population comprises mouse cells and the IgH locus is being targeted, the restriction endonuclease enzyme used is selected from DpnII and/or NlaIII.

Restriction endonucleases are selected upon the following criteria: 4 bp cutters are preferred to generate fragment sizes suitable for enrichment by magnetic beads. The restriction endonucleases must not cut anywhere within the J gene, or constant region, or 5' of the primers used in step (b) of the second aspect of the invention. Restriction endonucleases that generate overhangs are preferred because sticky-end ligation is more efficient than blunt-ended ligation. In human cells DpnII and/or NlaIII are also suitable for targeting the Igh locus. However there is a DpnII cut site within J2 leaving just 16 bp in which to locate a primer.

In one embodiment, the method comprises the use of a third restriction endonuclease enzyme. When present, the third restriction endonuclease enzyme will be specific for a region upstream of the V gene.

It will be appreciated that the sequencing method described herein comprises an Illumina sequencing method, such as the Illumina sequencing by synthesis (SBS) technology which is available from Illumina. When the Illumina sequencing technology is used, the procedure will typically comprise addition of adapter molecules to each end of the VDJ recombination product, e.g. following restriction endonuclease treatment in step (d) of the second aspect of the invention. Thus, in one embodiment the method additionally comprises the addition of a first adapter molecule to one end of the VDJ recombination product. In a particular embodiment, the method additionally comprises the addition of a first adapter molecule to one end of the VDJ recombination product following restriction endonuclease treatment. In a further embodiment, the first adapter is added to the VDJ recombination product by ligation. It will be appreciated that the adapter molecule will be selected depending upon the restriction endonuclease used. For example, when the restriction endonuclease used is NlaIII, the adapter molecule will comprise a complementary paired end with NlaIII. In one embodiment, when the restriction endonuclease used is NlaIII, the adapter molecule may be selected from SEQ ID NO: 5. In an alternative embodiment, when the restriction endonuclease used is DpnII, the adapter molecule may be selected from SEQ ID NO: 6.

In one embodiment, when sonication is used to fragment the DNA, the T-overhang adapter is ligated to the sonicated DNA following end repair and A-tailing. In a further embodiment, when sonication is used to fragment the DNA, the adapter molecule may be selected from SEQ ID NOS: 22 and 23.

In a further embodiment the method additionally comprises the addition of a second adapter molecule to a second end of the VDJ recombination product. In a further embodiment, the second adapter is incorporated into the VDJ recombination product by PCR. When the cell population comprises mouse cells, the primers for the addition of the second adaptor may be selected from SEQ ID NOS: 7 to 11 or 57 to 65. In a further embodiment, when the cell population comprises mouse cells, the primers for the addition of the second adaptor may be selected from SEQ ID NOS: 7 to 11.

In an alternative embodiment, when the cell population comprises human cells and the primers for the addition of the second adaptor are selected from SEQ ID NOS: 66 to 72.

The advantage of incorporating the second adapter by PCR is that the resultant amplified products will be free of the binding pair complexes if used for enrichment of the recombined VDJ products.

Step (d) of the first aspect of the invention (or step (e) of the second aspect of the invention) typically comprises the separation, or depletion, of the recombined VDJ digested fragments from the unrecombined J fragments by any suitable molecular biology depletion means. For example, the methodology described herein relates to primer extension (performed in an analogous manner to that described for step (c) of the second aspect of the invention) of oligonucleotides designed to portions present on the unrecombined J fragment but not on the recombined VDJ fragments. For example, in one embodiment step (d) of the first aspect of the invention (or step (e) of the second aspect of the invention) comprises the use of oligonucleotides specific to the upstream region of each of the 4 or 6 J genes on both strands. In a further embodiment, when the cell population comprises mouse cells, the oligonucleotides used in step (d) of the first aspect of the invention (or step (e) of the second aspect of the invention) may be selected from SEQ ID NOS: 12 to 19 or 24 to 34. In a yet further embodiment, when the cell population comprises mouse cells, the oligonucleotides used in step (d) of the first aspect of the invention (or step (e) of the second aspect of the invention) may be selected from SEQ ID NOS: 12 to 19.

In an alternative embodiment, when the cell population comprises human cells and the oligonucleotides used in step (d) of the first aspect of the invention (or step (e) of the second aspect of the invention) are selected from SEQ ID NOS: 35 to 46.

As previously described herein, in one embodiment, the primer additionally comprises one member of a binding pair. This embodiment provides the advantage of allowing depletion of the unrecombined J fragments over the recombined VDJ sequences. Examples of suitable binding pairs include biotin and streptavidin or an antigen and an antibody. In one embodiment, the primer additionally comprises biotin or streptavidin, such as biotin. It will be appreciated that depletion of a biotinylated fragment will require a streptavidin containing moiety, such as a magnetic bead containing streptavidin, for example streptavidin coupled Dynabeads.

Once the depletion step is complete, the resultant VDJ recombination products may then be sequenced. It will be appreciated that any sequencing analysis procedure may typically be used. In one embodiment, the sequencing step comprises standard Illumina 36 bp paired end sequencing. In an alternative embodiment, the sequencing step comprises Illumina MiSeq 250 bp single end sequencing.

When the Illumina sequencing technology is used, the procedure will typically require a sticky-end PCR reaction prior to sequence analysis in order to ensure sufficient binding to the flow cell. Such sticky-end PCR reactions may be conducted in accordance with the manufacturers protocol. When the method of the invention comprises sticky-end PCR, the primers may be selected from SEQ ID NOS: 20 and 21.

Alternatively, sequencing may require the addition of paired end adapters, e.g. for paired-end sequencing. These adapters may be used to attach to an Illumina flow cell. When the method of the invention comprises the use of paired-end sequencing, the primers may be selected from SEQ ID NOS: 73 to 85 or 98 to 106.

Data may be processed in accordance with four main steps. Firstly the paired end reads are classified according to J segment identity and restriction endonuclease (if used for DNA fragmentation). Secondly the classified reads are filtered to identify unique recombination events and to exclude unrecombined reads and PCR duplicates. Thirdly the reads are mapped to either the genome or to a virtual array of known V, D and J segment sequences to identify the recombined V or D segments in each read. Fourthly the number of reads assigned to each V or D segment are quantified and displayed as a bar chart similar to FIG. 7 or FIG. 8.

According to a further aspect of the invention, there is provided a kit for identifying VDJ recombination products which comprises instructions to use said kit in accordance with the methods described herein.

In one embodiment, the kit additionally comprises nucleic acid extraction reagents configured to obtain the nucleic acid sample required for step (a) of the method of the invention.

In one embodiment, the kit additionally comprises oligonucleotides or primers specific for a unique region within or immediately downstream of each of the J genes or within the constant region as defined herein. In a further embodiment, the kit additionally comprises oligonucleotides or primers specific for a unique region within or immediately downstream of each of the J genes as defined herein.

In one embodiment, the kit additionally comprises primer extension reagents configured to perform the primer extension process of step (c) of the second aspect of the invention.

In one embodiment, the kit additionally comprises one or more restriction endonuclease enzymes as defined herein.

In one embodiment, the kit additionally comprises a computer readable storage medium configured to process the sequencing data obtained and generate a visual representation of VDJ recombination frequencies in the sample.

Due to the unbiased nature of the assay any DNA sequence that has been recombined with a J segment can be identified. Several V genes have been found to be recombined by inversion of the intervening DNA sequence rather than the typical deletion. VDJ recombination by inversion generates non-functional VD recombined products, however these Igh specific products have not been described in the literature before. Similarly the assay is also able to detect translocations, where aberrant recombination has taken place between a J gene and another region of the genome. Therefore the assay has the potential to identify common Igh translocation partners. Thus, according to a further aspect of the invention, there is provided a VDJ recombination product obtainable by the method as described herein.

It will be appreciated that analysis of the VDJ repertoire of an individual as described herein can be used to monitor immunodeficiency disorders. According to a further aspect of the invention, there is provided a VDJ recombination product or a method of identifying a VDJ recombination product as described herein for use in monitoring an immunodeficiency disorder. In one embodiment, the immunodeficiency disorder is selected from a lymphoma or leukemia. In a further embodiment, the immunodeficiency disorder is selected from a clinically defined immunodeficiency disorder. In a yet further embodiment, the immunodeficiency disorder is selected from an ageing-related impairment of immune function.

By monitoring VDJ recombination products in accordance with methods of the invention, patient care can be tailored precisely to match the needs determined by the disorder and the pharmacogenomic profile of the patient.

The invention will now be described in more detail with reference to the following non-limiting Examples:

Example 1

VDJ Recombination Product Identification Method in Mouse B Cells Using Restriction Endonucleases (A) Methods
(i) Primer Extension Using Biotinylated J Segment-Specific Oligonucleotides ~7.5 µg of DNA was isolated from ~2×10$^6$ FACS sorted fraction B/C B cells and was divided into 8 aliquots to give ~1 µg per reaction. Primer extension reactions were assembled in 50 µl volumes using 2 U of Vent (exo-) DNA polymerase (NEB) in the supplied 1× reaction buffer and 200 µm of dNTPs. A cocktail of 4 biotinylated oligonucleotides were used in the reaction and they were designed to anneal to each of the four J segments in the Igh locus:

```
J segment biotinylated oligonucleotides
                                 (SEQ ID NO: 1)
J1 Rev Bio      *-AGCCAGCTTACCTGAGGAGAC (SEQ ID NO: 2)
J2 Rev Bio      *-GAGAGGTTGTAAGGACTCACCTG (SEQ ID NO: 3)
J3 Rev Bio      *-AGTTAGGACTCACCTGCAGAGAC (SEQ ID NO: 4)
J4 Rev Bio      *-AGGCCATTCTTACCTGAGGAG
wherein * refers to the biotin moiety
```

The primer extension reaction was denatured at 94° C. for 4 mins, annealed at 60° C. for 2 mins, and extended at 72° C. for 10 mins, then chilled on ice. The primer extension reactions were combined and magnetically purified using 720 µl of Agencourt AMPure XP SPRI beads (Beckman Coulter) according to the manufacturers protocol, and eluted into 208 µl of water.

(ii) Restriction Endonuclease Digestion

The sample was mixed thoroughly and divided into 2 tubes, 1.2 µl of BSA, 12 µl of the appropriate NEB digestion buffer, and 20 units of either DpnII or NlaIII (NEB) restriction endonucleases were added to each tube. The samples were incubated for 3 hours at 37° C. on a Thermomixer (Eppendorf) at 1200 rpm. Following digestion the reactions were purified using 216 µl of SPRI beads and eluted into 50 µl of water.

(iii) Enrichment of VDJ Recombined DNA

The biotinylated VDJ recombined DNA fragments were enriched using streptavidin coupled Dynabeads from the kilobaseBINDER kit (Invitrogen). 10 µl aliquots of Dynabeads were prepared according to the manufacturers protocol, to which the 50 µl DNA samples were added and incubated overnight at 20° C. on a Thermomixer at 1200 rpm.

The samples were placed on a magnet for 5 mins and the supernatant was removed and discarded. The pellet was washed twice in 100 µl of the kilobaseBINDER kit wash buffer, and washed once in 100 µl of 1×NEB digestion buffers appropriate to either DpnII or NlaIII. The pellets were resuspended in 1×NEB digestion buffer and 0.5 µl of either DpnII or NlaIII was added and incubated at 37° C. for an hour to ensure complete digestion.

(iv) Incorporation of a First Illumina Adapter by Ligation

The digestion reactions were cleaned up by removal of the supernatant on a magnet, followed by 2 washes of 100 µl of kilobaseBINDER kit wash buffer, and one wash in 100 µl of 10 mM Tris-Cl, pH 8.5. The beads were resuspended in 50 µl of 1×NEB ligase buffer and incubated at 55° C. for 5 minutes, then rapidly chilled on ice.

In addition the NlaIII-Illumina adapter, and DpnII-Illumina adapter stocks were also incubated at 55° C. for 5 minutes and rapidly chilled on ice. The beads were placed on a magnet and the supernatant was removed. To each tube 33 µl of water, 4 µl of 10×NEB ligase buffer, and 1 µl (2000 U) of T4 DNA ligase (NEB) was added along with 2 µl (200 pmol) of either the NlaIII-, or DpnII-Illumina adapter appropriate to the sample:

```
Paired-end adapter 1
PE Adapter 1 - NlaIII
                                 (SEQ ID NO: 5)
ACACTCTTTCCCTACACGACGCTCTTCCGATCTCATGTGTGAGAAAGGGA TGTGCTGCGAGAAGGCTAGAp PE Adapter 1 - DpnII
                                 (SEQ ID NO: 6)
ACACTCTTTCCCTACACGACGCTCTTCCGATCTTGTGAGAAAGGGATGTG CTGCGAGAAGGCTAGACTAGp
```

The ligation reaction was incubated for 2 hours at room temperature on a rotating wheel. The ligation reaction was cleaned up by removal of the supernatant on a magnet followed by 2 washes of 100 µl of kilobaseBINDER kit wash buffer, and one wash in 100 µl of 10 mM Tris-Cl, pH 8.5.

(v) Incorporation of the Second Illumina Adapter by PCR

The samples were placed on a magnet and the previous Tris-Cl wash was removed.

The beads were washed once with 50 µl of 1×PCR mix (1× buffer and 200 µM of each dNTP). Each sample was to be divided into 8 PCR reactions so sufficient PCR master mixes were prepared. Master mix 1 contained the following per reaction: 21 µl of water, 1 µl of 10 mM dNTP mix, 1.5 µl of 10 µM Illumina paired end adaptor 1 forward primer, and 1.5 µl of a 10 µM mix of 4 J segment specific reverse primers incorporating the Illumina paired end adapter 2 sequence at the 5' end.

PCR primers for incorporation of paired end adapter 2
PE adaptor 1 forward (SEQ ID NO: 7)
ACACTCTTTCCCTACACGACGCTCTTCCGATCT J1 PE PCR adapter 2 reverse (SEQ ID NO: 8)
CTCGGCATTCCTGCTGAACCGCTCTTCCGATCTCCCAGACATCGAAGTAC

CAG

J2 PE PCR adapter 2 reverse (SEQ ID NO: 9)
CTCGGCATTCCTGCTGAACCGCTCTTCCGATCTTTGGCCCCAGTAGTCAA

AG

J3 PE PCR adapter 2 reverse (SEQ ID NO: 10)
CTCGGCATTCCTGCTGAACCGCTCTTCCGATCTTGGCCCCAGTAAGCAAA

C

J4 PE PCR adapter 2 reverse (SEQ ID NO: 11)
CTCGGCATTCCTGCTGAACCGCTCTTCCGATCTCCCAGTAGTCCATAGC

ATAG

Master mix 2 contained the following per reaction: 19.25 μl of water, 5 μl of 10× Expand high fidelity buffer (Roche) and 0.75 μl of Expand high fidelity Taq (Roche, 2.6 U).

The samples were placed on a magnet and the supernatant was removed. The beads were resuspended in 200 μl of Master mix 1 and 25 μl was aliquoted into 8 PCR tubes. 25 μl of Master mix 2 was added to each tube and mixed. The PCR reaction was initially denatured at 94° C. for 2 minutes, but during the PCR cycling was denatured for 15 seconds. The primers were annealed at 60° C. for 30 seconds, and elongated for 1 minute at 72° C. The PCR was cycled 15 times followed by a final elongation step of 5 minutes at 72° C. The 8 PCR reactions were pooled into a single Eppendorf and placed on the magnet. The 400 μl supernatant was removed and placed in a fresh tube and the beads were discarded. The pooled PCR reaction was cleaned up using 720 μl of SPRI beads according to the manufacturers protocol and eluted into 200 μl of water.

(vi) Depletion of Unrecombined J Segments

Each 200 μl sample was divided into eight 25 μl aliquots and placed into PCR tubes.

To each aliquot a primer extension reaction was assembled using 5 μl of the supplied NEB buffer, 1 μl of 10 mM dNTP mix, 1 μl (2 U) of Vent (exo-) DNA polymerase (NEB), 17 μl of water and 1 μl of a 10 μM cocktail of 8 biotinylated oligos specific to the upstream regions of each of the 4 J segments on both strands:

```
Depletion biotinylated oligonucleotides
                                  (SEQ ID NO: 12)
    J1 dep bio F    *-ATCTGAGTTTCTGAGGCTTG (SEQ ID NO: 13)
    J1 dep bio R    *-AAAACTCTCTCCACATCCTG (SEQ ID NO: 14)
    J2 dep bio F    *-CTAAAGGGGTCTATGATAGTGTG (SEQ ID NO: 15)
    J2 dep bio R    *-GTGTACAAAAACCCATCTACC (SEQ ID NO: 16)
    J3 dep bio F    *-CATTGTTGTCACAATGTGC (SEQ ID NO: 17)
    J3 dep bio R    *-TTAGACCCCTGACAATAAATG (SEQ ID NO: 18)
    J4 dep bio F    *-GTGGAACAATGACTTGAATG (SEQ ID NO: 19)
    J4 dep bio R    *-TGGGCAACTCAGACATTAT
    wherein * refers to the biotin moiety
```

The primer extension reaction was denatured at 94° C. for 4 mins, annealed at 55° C. for 2 mins, and extended at 72° C. for 10 mins, then chilled on ice. The 8 primer extension reactions were pooled and magnetically purified using 720 μl of SPRI beads according to the manufacturers protocol, and eluted into 50 μl of water.

The biotinylated unrecombined DNA fragments were depleted using streptavidin coupled Dynabeads from the kilobaseBINDER kit (Invitrogen). 10 μl aliquots of Dynabeads were prepared according to the manufacturers protocol, to which the 50 μl DNA samples were added and incubated overnight at 20° C. on a Thermomixer at 1200 rpm. The samples were placed on a magnet for 5 mins and the supernatant was removed and placed in a fresh tube, the beads containing the unrecombined fragments were discarded. The depleted samples were magnetically purified using 108 μl of SPRI beads according to the manufacturers protocol, and eluted into 50 μl of water.

(vii) Illumina Size Selection

The DpnII and NlaIII samples were combined into a single tube, gel-loading buffer was added and the combined sample was run out on a 1.5% agarose TAE gel. The sample was sized selected by excision of a gel slice extending from 100 to 1000 bp.

The sample was isolated from the gel slice using the QIAGEN gel extraction kit according to the manufacturers protocol and was eluted in 50 μl of elution buffer.

(viii) Sticky End PCR for Illumina Flowcell Binding

Sufficient PCR Master mixes were prepared for 5 reactions. Master mix 1 contained the following per reaction: 11 μl of water, 1 μl of 10 mM dNTP mix, 1.5 μl of 10 μM Illumina paired end PCR forward primer, and 1.5 μl of 10 μM Illumina paired end PCR reverse primer.

```
Sticky-end PCR primers
Illumina PE PCR forward
                                  (SEQ ID NO: 20)
AATGATACGGCGACCACCGAGATCTACACTCTTTCCCTACACGACGCTCT

TCCGATCT

Illumina PE PCR reverse
                                  (SEQ ID NO: 21)
CAAGCAGAAGACGGCATACGAGATCGGTCTCGGCATTCCTGCTGAACCGC

TCTTCCGATCT
```

Master mix 2 contained the following per reaction: 19.25 μl of water, 5 μl of 10× Expand high fidelity buffer (Roche) and 0.75 μl of Expand high fidelity Taq (Roche, 2.6 U).

75 μl of Master mix 1 was combined with the 50 μl sample, mixed and aliquoted into 5 PCR tubes. To each tube 25 μl of Master mix 2 was added and mixed. The PCR reaction was initially denatured at 94° C. for 2 minutes, but during the PCR cycling was denatured for 15 seconds. The primers were annealed and elongated at 72° C. for 1 minute. The PCR was cycled 10 times followed by a final elongation step of 5 minutes at 72° C. The PCR reactions were pooled and magnetically purified using 450 μl of SPRI beads according to the manufacturers protocol, and eluted into 60 µl of 10 mM Tris-Cl, pH 8.5.

(ix) Illumina Sequencing

The sample was submitted for standard Illumina 36 bp paired end sequencing.

(B) Results

Figure 7:
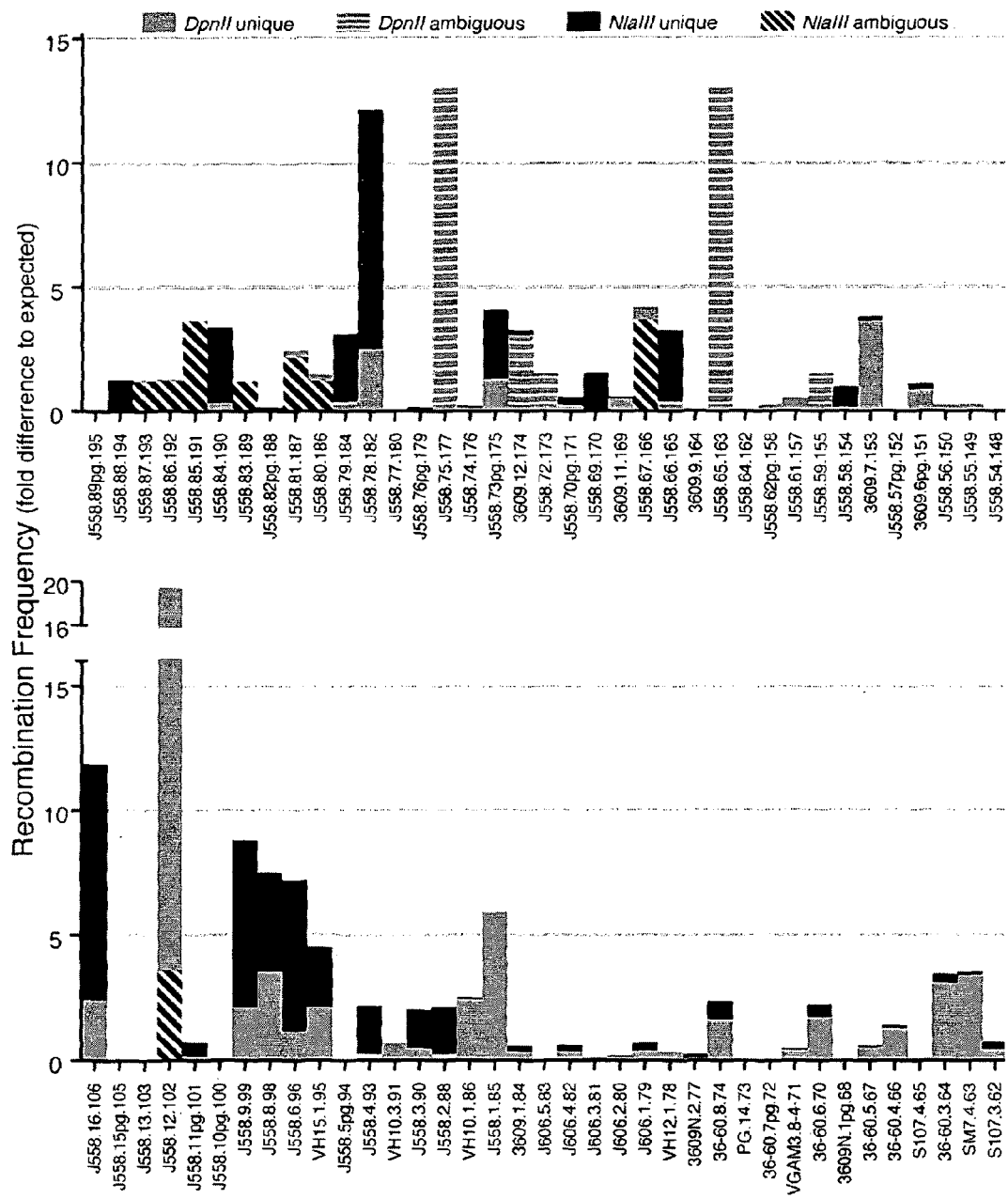
FIG. 7 provides a detailed picture of usage of each one of 195 individual V genes analysed by the method of the invention in accordance with the methodology described in Example 1.

The results of the analysis are shown in FIG. 7 which depicts the recombination frequency data of V genes in the mouse Igh locus. All detectable V genes are shown in locus order on the x-axis, which has been split into two due to space constraints. The DpnII and NlaIII datasets have been normalized by dividing the total number of reads per dataset by the number of V segments detectable with that restriction enzyme giving number of reads per segment expected if the reads were evenly distributed. Finally, the number of reads observed for each V segment was divided by that expected number giving fold difference between number of reads observed compared to number of reads expected. A value of 1 corresponds to the number of reads expected if reads were evenly distributed.

Example 2

VDJ Recombination Product Identification Method in Mouse B Cells Using Sonication (A) Methods
(i) Sample Material Bone marrow taken from 15 mice generally yields approximately $5 \times 10^6$ fraction B/C VDJ recombined B cells following MACS depletion & FACS sorting. Approximately 16 µg of DNA is typically isolated from this number of cells using the Qiagen DNeasy kit. For splenic B cells, deplete spleen of T cells, activated B cells and erythrocytes using CD43 biotin (1:1000) and Ter119 (1:400). One spleen typically gives $6-8 \times 10^7$ cells at greater than 90% purity from $1-1.5 \times 10^8$ starting cells. $10^7$ cells makes over 20 µg DNA using the Qiagen DNeasy kit. Therefore, taking 10 µg through is equivalent to $4-5 \times 10^6$ cells. After eluting the DNA from the kit in buffer AE, precipitate with EtOH/NaOAc and spool out into 70% EtOH wash then into fresh tube. Resuspend immediately in the same volume of water—very little DNA is lost as a result of this (less than 5%). Nanodrop is used to determine DNA concentration and yield.

(ii) Fragmentation & Repair

DNA is fragmented using the Covaris E220 system using the manufacturer's protocol to generate 500 bp peak fragments. The machine requires at least 1 hour of pre-cooling and degassing before use.

1. Resuspend up to 10 µg of DNA in 130 µl of water and transfer to Covaris crimp cap microtube (Cat No. 520052). Nanodrop should be relatively accurate for this DNA but you may want to quantify the DNA using picogreen assay.

2. Place tubes in Covaris E220 and run the following program for 500 bp:

| | |
|---|---|
| Peak Incident Power (W) | 105 |
| Duty Factor | 5% |
| Cycles per Burst | 200 |
| Treatment time (s) | 80 |
| Temperature (° C.) | 7 |
| Water Level | 6 |

3. Transfer sample from microtube to 1.5 ml eppendorf. Run a small amount to check size although the migration kinetics of the DNA at this stage may be different to the ladder due to ragged ends.

4. End repair DNA using the mix below:
130 µl DNA
16 µl 10× T4 DNA ligase buffer (use fresh aliquot)
4 µl 10 mM dNTP mix
5 µl T4 DNA polymerase (NEB)
1 µl Klenow (NEB)
5 µl T4 PNK (NEB)
Total: 161 µl volume
Incubate at 20° C. for 30 minutes.

5. Purify reaction using Qiagen QIAquick columns using PCR purification protocol and elute in 50 µl buffer EB.

(iv) PE1 Adapter Ligation

6. Create A-tails on the end of the repaired DNA using the mix below:
50 µl of end repaired DNA
6 µl 10×NEB buffer 2
1 µl 10 mM dATP
3 µl Klenow (exo-) (NEB)
Total: 60 µl volume
Incubate at 37° C. for 30 minutes.

7. Purify reaction using Qiagen QIAquick columns using PCR purification protocol and elute in 30 µl water twice.

8. Ligate Adapter oligo mix using the mix below:
30 µl of A-tailed DNA
5 µl 10× T4 DNA ligase buffer (NEB—use fresh aliquot)
4/8 µl Adapter oligo mix (50 pmol)
5 µl T4 DNA ligase 2000 U (NEB)
Total: 50 µl volume
Incubate overnight at 16° C.

Adapter mix uses 2 oligos: "DpnII adapter F" & "Rev PE both adapter", which anneal together to create an asymmetric PE1 adapter:

| PCR primers for Adapter oligo mix | | |
|---|---|---|
| Primer | Sequence | SEQ ID NO |
| DpnII adapter F | ACACTCTTTCCCTACACGACGCTCTTCCGATC*T | 22 |
| Rev PE both adapter | CGAGAAGGCTAG[Phos] | 23 | wherein * refers to biotin moiety and [Phos] refers to a phosphorothioate moiety Working stock of 100 µM for each oligo are mixed together to give 50 µM of adaptor. There is no need to heat and cool these, just mix equimolar amounts and use. 4 µl of adaptor used in reaction=200 pmol which is approximately 6.67:1 ratio of adaptor ends (1×) to DNA ends (2×) (5 µg of 500 bp fragments=15 pmol×2=30 pmol). For 10 µg DNA use 8 µl adaptor.

9. Purify reaction using Qiagen QIAquick columns using PCR purification protocol, elute in 50 µl water. When 1 µl of this on a gel there was a shift of all fragments of approximately 40-50 bp indicating highly efficient adapter ligation.

(v) Depletion of Unrecombined J Segments

10. Primer extension using biotinylated oligos annealing to upstream regions of each J segment. Split sample into separate primer extension reactions not exceeding 1 µg DNA per reaction. For example, 8× reactions use less than 1 µg per reaction accounting for loss of DNA through cleanup.

5 µl 10× ThermoPol reaction buffer
1 µl dNTPs (10 mM each)
1 µl Biotinylated primers (10 mM mix)
1 µl Vent exo- (NEB)
~25 µl DNA (up to 2.5 µg DNA per reaction)
~17 µl water to 50 µl
Total: 50 µl volume Thermal cycler conditions: 95° C. for 4 minutes, 55° C. for 5 minutes, 72° C. for 15 minutes, 4° C. pause.

A mixture of 8 biotinylated primers are used with Tms between 57.4° C. to 59.4° C.:

Depletion biotinylated primers

| Target | Primer | Sequence | SEQ ID NO |
|---|---|---|---|
| Mouse IgH | J1 dep F new | *-ACAGAGGCAGAACAGAGACT | 24 |
| | J1 dep R | *-AAAACTCTCTCCACATCCTG | 13 |
| | J2 dep F | *-CTAAAGGGGTCTATGATAGTGTG | 14 |
| | J2 dep R | *-GTGTACAAAAACCCATCTACC | 15 |
| | J3 dep F | *-CATTGTTGTCACAATGTGC | 16 |
| | J3 dep R | *-TTAGACCCCTGACAATAAATG | 17 |
| | J4 dep F new | *-AGAGGAAAAATCCACTATTGTG | 25 |
| | J4 dep R new | *-CCAGAGTCTGACTAGAATCACC | 26 |
| Mouse IgK | Jk1 F Dep | *-TACAGCCAGACAGTGGAGTAC | 27 |
| | Jk1 R Dep | *-CCTCACTGAAGAGGAACAGA | 28 |
| | Jk2 F Dep | *-TTGAGTGAAGGGACACCA | 29 |
| | Jk2 R Dep | *-CCCATACAAAAACTGAGCAT | 30 |
| | Jk4 F Dep | *-CTGAACTTAGCCTATCTAACTGG | 31 |
| | Jk4 R Dep | *-TTTACAAAAACCTGCCTGAG | 32 |
| | Jk5 F Dep | *-GCATGTCATAGTCCTCACTGT | 33 |
| | Jk5 R Dep | *-TCTCTACAAAAACCTGCCTG | 34 |
| Human IgH | Hu J1 F Dep | *-CAGGGCTGACTCACCGTG | 35 |
| | Hu J1 R Dep | *-CAGAAACCCACAGCCCG | 36 |
| | Hu J2 F Dep | *-GTGTTTTTGTATGGGAGAAGCAG | 37 |
| | Hu J2 R Dep | *-CACAGCCTCTGCCCTCCT | 38 |
| | Hu J3 F Dep | *-ACGGGCACAGGTTTGTGTC | 39 |
| | Hu J3 R Dep | *-GTCCCTGTTCCTGCCCAG | 40 |
| | Hu J4 F Dep | *-GTCGGAGAGTCAGGTTTTTGTG | 41 |
| | Hu J4 R Dep | *-AGTCACATTGTGGGAGGCC | 42 |
| | Hu J5 F Dep | *-GTCTGAGAGGGTCCCAGGG | 43 |
| | Hu J5 R Dep | *-GTGACAACAATGCCAGGACC | 44 |
| | Hu J6 F Dep | *-GGTGAGGATGGACATTCTGC | 45 |
| | Hu J6 R Dep | *-CAGCCACCCAGAGACCTTC | 46 | wherein * refers to the biotin moiety

11. Pool multiple reactions and purify using Qiagen QIAquick columns using PCR purification protocol. Use pH indicator in buffer PB (i.e. PBI). Add 10 µl 3M NaOAc and elute in 40 µl water.

12. Prepare Dynabeads MyOne Streptavidin C1 beads (Invitrogen). Vortex Dynabead stock, transfer 20 µl to eppendorf, add 1 ml 1× B&W buffer (Binding & Washing), mix, place tube on magnet for 2 mins, discard supernatant. Resuspend beads in 20 µl of 1× B&W buffer, place on magnet and discard supernatant. Repeat 20 µl wash a total of 3 times. Resuspend beads in 40 µl of 2× B&W buffer.

2× B (Binding & Washing) buffer

| Final concentration | Stock | Amount for 50 ml |
|---|---|---|
| 10 mM Tris-HCl (pH 7.5) | 1M | 500 µl |
| 1 mM EDTA | 0.5M | 100 µl |
| 2M NaCl | 5M | 20 ml |
| 0.05% Tween-20 | 100% | 25 µl |
| Water | — | 29.4 ml |

13. Add 40 µl of DNA sample from step 11 to beads, mix and incubate for 60 minutes, or overnight, on rotator at room temperature.

14. Place sample on magnet for 5 minutes, pipette supernatant into clean eppendorf. Wash beads by resuspending in 80 µl EB buffer, place on magnet for 5 minutes and transfer supernatant to the same tube as before.

15. Purify reaction using Qiagen QIAquick columns using PCR purification protocol, elute in 50 µl water.

(vi) Enrichment of VDJ Recombined Fragments

16. Primer extension using biotinylated oligos annealing within each J segment, approximately 8 bp inset from the 5' end. Split sample into separate primer extension reactions, not exceeding 1 µg DNA per reaction.

5 µl 10× ThermoPol reaction buffer
1 µl dNTPs (10 mM each)
1 µl Biotinylated primers (10 mM mix)
1 µl Vent exo- (NEB)
~25 µl DNA (up to 2.5 µg DNA per reaction)
~17 µl water to 50 µl
Total: 50 µl volume Thermal cycler conditions: 95° C. for 4 minutes, 59° C. for 5 minutes, 72° C. for 15 minutes, 4° C. pause.

A mixture of biotinylated primers are used depending on the cell population. Tms are between 62.7° C. to 63.7° C.:

Biotinylated primers for enrichment of VDJ recombined fragments

| Target | Primer | Sequence | SEQ ID NO |
|---|---|---|---|
| Mouse IgH | J1 Rev Bio | *-AGCCAGCTTACCTGAGGAGAC | 1 |
| | J2 Rev Bio | *-GAGAGGTTGTAAGGACTCACCTG | 2 |
| | J3 Rev Bio | *-AGTTAGGACTCACCTGCAGAGAC | 3 |
| | J4 Rev Bio | *-AGGCCATTCTTACCTGAGGAG | 4 |
| Mouse IgK | Jk1 R Bio | *-GAAAGAGACTTTGGATTCTACTTACG | 47 |
| | Jk2 R Bio | *-GAACAAGAGTTGAGAAGACTACTTACG | 48 |
| | Jk3 R Bio | *-CACAAGTAAATGAGCAAAAGTCTACTT | 49 |
| | Jk4 R Bio | *-AAAGATGAGAAAAGTGTACTTACGTTTC | 50 |
| Human IgH | Hu J1 R Bio | *-CCAGACAGCAGACTCACCTG | 51 |
| | Hu J2 R Bio | *-TGCAGTGGGACTCACCTG | 52 |
| | Hu J3 R Bio | *-AGAAGGAAAGCCATCTTACCTG | 53 |
| | Hu J4 R Bio | *-CAGGAGAGAGGTTGTGAGGACT | 54 |
| | Hu J5 R Bio | *-AGGGGGTGGTGAGGACTC | 55 |
| | Hu J6 R Bio | *-CCATTCTTACCTGAGGAGACG | 56 | wherein * refers to the biotin moiety.

17. Pool multiple reactions and purify using Qiagen QIAquick columns using PCR purification protocol. Use pH indicator in buffer PB (i.e. PBI) and elute in 40 µl water.

18. Prepare Dynabeads MyOne Streptavidin C1 beads (Invitrogen) as before (see step 12).

19. Combine the DNA sample with the prepared Dynabeads, mix and incubate overnight on rotator at room temperature.

20. Place sample on magnet for 5 minutes, keep and clean up supernatant with Qiagen kit as depleted fraction. Wash beads twice in 100 µl 1× B&W buffer, and wash once in 100 µl EB (Qiagen). Resuspend beads in 46 µl buffer EB.

(vii) Incorporation of PE2 Adapter by PCR

21. PCR using Pwo master (Roche) with a mixture of four J reverse primers 10 bp downstream of the unaltered recombination junction with PE2 sequence at the 5' end and a single forward primer annealing to the PE1 sequence in the ligated adapter. Each sample is divided into four separate 25 µl PCR reactions to increase library diversity. A negative, using water instead of DNA, is included to be used as a control for PCR contamination.

| Mix | x5 |
|---|---|
| 12.5 µl Pwo master | 62.5 µl |
| 0.5 µl F primer (10 µM PE1 short) | 2.5 µl |
| 0.5 µl R primer mix (10 µM J1-J4 PE2) | 2.5 µl |
| 11.5 µl DNA on beads (step 20) | 46 µl |
| Total: 25 µl volume | 125 µl |

Place on the PTC100 using the following conditions:

94° C. for 2 minutes, 15 cycles of: 94° C. for 15 seconds, 61° C. for 30 seconds, 72° C. for 45 seconds, followed by 72° C. for 5 minutes, and 4° C. pause. The final number of PCR cycles required will need titrating to achieve optimal amplification, for example 10, 12 or 15 cycles. It is considered to be best to do more cycles in the first round than the second (for example, 15× 1st round, 7× 2nd round). Ensure these primers are at least HPLC, ideally PAGE purified. Short PE1 primer Tm: 68.5° C.; J primers Tm range: 68.7-69.8° C.

Primer sequences for incorporation of PE adapters

| Target | Primer | Sequence | SEQ ID NO |
|---|---|---|---|
| Mouse IgH | Short primer 1.0.1 | ACACTCTTTCCCTACACGACGCTCpT | 57 |
| | J1.10 PE2 PCR | GTGACTGGAGTTCAGACGTGTGCTCTTCCGA TCTCCCTGTGCCCCAGACATCGApA | 58 |
| | J2.10 PE2 PCR | GTGACTGGAGTTCAGACGTGTGCTCTTCCGA TCTAGTGGTGCCTTGGCCCCAGTApG | 59 |
| | J3.10 PE2 PCR | GTGACTGGAGTTCAGACGTGTGCTCTTCCGA TCTACCAGAGTCCCTTGGCCCCAGTApA | 60 |
| | J4.10 PE2 PCR | GTGACTGGAGTTCAGACGTGTGCTCTTCCGA TCTTGAGGTTCCTTGACCCCAGTAGTCCATpA | 61 |
| Mouse IgK | Jk1 PE2 PCR | GTGACTGGAGTTCAGACGTGTGCTCTTCCGA TCTTTTTGATTTCCAGCTTGGTGCCTCpC | 62 |
| | Jk2 PE2 PCR | GTGACTGGAGTTCAGACGTGTGCTCTTCCGA TCTTTTTATTTCCAGCTTGGTCCCCCCpT | 63 |
| | Jk3 PE2 PCR | GTGACTGGAGTTCAGACGTGTGCTCTTCCGA TCTCGTTTTATTTCCAACTTTGTCCCCGpA | 64 |

-continued

Primer sequences for incorporation of PE adapters

| Target | Primer | Sequence | SEQ ID NO |
|---|---|---|---|
| | Jk4 PE2 PCR | GTGACTGGAGTTCAGACGTGTGCTCTTCCGA TCTCAGCTCCAGCTTGGTCCCAGpC | 65 |
| Human IgH | Hu J1 PE2 PCR | GTGACTGGAGTTCAGACGTGTGCTCTTCCGA TCTGGTGCCCTGGCCCCAGTpG | 66 |
| | Hu J2 PE2 PCR | GTGACTGGAGTTCAGACGTGTGCTCTTCCGA TCTGGTGCCACGGCCCCAGAGpA | 67 |
| | Hu J3 PE2 PCR | GTGACTGGAGTTCAGACGTGTGCTCTTCCGA TCTACCATTGTCCCTTGGCCCCApG | 68 |
| | Hu J4 PE2 PCR | GTGACTGGAGTTCAGACGTGTGCTCTTCCGA TCTGACCAGGGTYCCYTGGCCCpC | 69 |
| | Hu J5 PE2 PCR | GTGACTGGAGTTCAGACGTGTGCTCTTCCGA TCTCAGGGTTCCYTGGCCCCAGpG | 70 |
| | Hu J6 PE2 PCR.1 | GTGACTGGAGTTCAGACGTGTGCTCTTCCGA TCTCCTTTGCCCCAGACGTCCATGTAGpT | 71 |
| | Hu J6 PE2 PCR.2 | GTGACTGGAGTTCAGACGTGTGCTCTTCCGA TCTTKSCCCCAGACGTCCATACCGpT | 72 | wherein p refers to a phosphorothioate bond

22. Pool the 4 separate PCR reactions into a single 1.5 ml tube. Place on magnet for 5 minutes pipette the supernatant containing the PE1-VDJ-PE2 products of interest to a new tube.

23. Wash beads once in 30 µl buffer EB, and add supernatant to the previous supernatant. Keep the beads as PCR can be attempted again on these but first do 2× 1 ml washes with water to remove any residual PCR products and resuspend in 46 µl EB and keep frozen.

24. Purify and size select PCR reaction using 1× volume SPRI/Seramag beads (will be approximately 120 µl). This removes primers/primer dimers and fragments less than 200 bp. Binding capacity of SPRI beads is 3 µg/µl and they are suspended in 20% PEG-8000, 2.5M NaCl (see, http://core-genomics.blogspot.co.uk/2012/04/how-do-spri-beads-work.html). Since the binding capacity is so great, it may be possible to dilute the beads down in this buffer to make them go further without affecting capture efficiency. Add beads, mix thoroughly by pipetting, incubate at room temp for 10 minutes or more, place on magnet for 5 minutes and discard supernatant. Wash twice with 500 µl fresh 70% EtOH, keeping the sample on the magnet. Do not resuspend the beads. Remove final EtOH wash, air-dry bead pellet partially. Remove tube from magnet and resuspend beads thoroughly in 46 µl buffer EB. Place tube back on magnet for 2 minutes and transfer supernatant containing purified and size selected PCR to fresh tube.

(viii) Incorporation of Flowcell Binding & Barcoding Sequences by PCR

25. PCR using Pwo master (Roche) with universal Flowcell PE1 primer in combination with one of eight index primers+PE2 per sample. Each sample is divided into four separate 25 µl PCR reactions to increase library diversity. Include negative control using 11.5 µl water instead of DNA.

| Mix | | x5 |
| --- | --- | --- |
| 12.5 µl Pwo master | | 62.5 µl |
| 0.5 µl F primer (10 µM Flowcell PE1) | | 2.5 µl |
| 0.5 µl R primer (10 µM Flowcell index PE2) | | 2.5 µl |
| 11.5 µl DNA (1st round PCR) | | 46 µl |
| Total: 25 µl volume | | 125 µl |

Place on the PTC100 using the following conditions:

94° C. for 2 minutes, 7 cycles of: 94° C. for 15 seconds, 55° C. for 30 seconds, 72° C. for 45 seconds, followed by 72° C. for 5 minutes, and 4° C. pause. The final number of PCR cycles will require titration to achieve optimal amplification but it may be good to keep the number of cycles in the second round PCR low, for example 5 or 7. Tms of regions annealing to target are 58.2° C. for PE1, and 61.9° C. for PE2.

Primers should be at least HPLC, preferably PAGE purified.

| Primers for incorporation of flowcell binding & barcoding sequences by PCR | | |
| --- | --- | --- |
| Primer | Sequence | SEQ ID NO |
| Flowcell PE1 | AATGATACGGCGACCACCGAGATCTACACTCTTTCCCTACACGAC | 73 |
| Flowcell PE2 Index 1 | CAAGCAGAAGACGGCATACGAGATCGTGATGTGACTGGAGTTCAGACGTGT | 74 |
| Flowcell PE2 Index 2 | CAAGCAGAAGACGGCATACGAGATACATCGGTGACTGGAGTTCAGACGTGT | 75 |
| Flowcell PE2 Index 3 | CAAGCAGAAGACGGCATACGAGATGCCTAAGTGACTGGAGTTCAGACGTGT | 76 |
| Flowcell PE2 Index 4 | CAAGCAGAAGACGGCATACGAGATTGGTCAGTGACTGGAGTTCAGACGTGT | 77 |
| Flowcell PE2 Index 5 | CAAGCAGAAGACGGCATACGAGATCACTGTGTGACTGGAGTTCAGACGTGT | 78 |
| Flowcell PE2 Index 6 | CAAGCAGAAGACGGCATACGAGATATTGGCGTGACTGGAGTTCAGACGTGT | 79 |
| Flowcell PE2 Index 7 | CAAGCAGAAGACGGCATACGAGATGATCTGGTGACTGGAGTTCAGACGTGT | 80 |
| Flowcell PE2 Index 8 | CAAGCAGAAGACGGCATACGAGATTCAAGTGTGACTGGAGTTCAGACGTGT | 81 |
| Flowcell PE2 Index 9 | CAAGCAGAAGACGGCATACGAGATCTGATCGTGACTGGAGTTCAGACGTGT | 82 |
| Flowcell PE2 Index 10 | CAAGCAGAAGACGGCATACGAGATAAGCTAGTGACTGGAGTTCAGACGTGT | 83 |
| Flowcell PE2 Index 11 | CAAGCAGAAGACGGCATACGAGATGTAGCCGTGACTGGAGTTCAGACGTGT | 84 |
| Flowcell PE2 Index 12 | CAAGCAGAAGACGGCATACGAGATTACAAGGTGACTGGAGTTCAGACGTGT | 85 |

26. Purify and size select PCR reaction using 1× volume Ampure XP (SPRI) beads as in 24. Elute in 40 µl EB. Ideally should be approximately 40-50 ng of the final library.

27. Determine concentration by picogreen. Run 2 µl out on a gel and perform QC PCRs checking for the presence of VDJ recombined products (e.g. VJ558.F to JR) and absence of non-Igh genes (e.g. B2M). Analyse enrichment of V-DJ and D-J products using J558FR3.F QPCR-J4.R QPCR assay and DSP/DFL.F-J4.R QPCR in SYBR real-time, comparing library with sonicated input DNA (for example, using sonicated spleen DNA as a control). Analyse depletion of unrecombined J region and non-Igh sequences using SYBR real-time PCR. For IgH J region use J3-J4 new int.F-mu0r2=141 bp (IgH J)—this region will be lost if depletion has successfully occurred. For non-Igh, B2M or actin can be used.

28. Bioanalyse results and perform QPCR in order to generate data.

(B) Results

The results of the analysis are shown in FIG. 8 which depicts the recombination frequency data of V genes in the mouse Igh locus. All V genes are shown in locus order on the x-axis, which has been split into four due to space constraints. Each V gene on the X axis is depicted by 3 bars representing the results from 3 biological replicates of mouse proB cells. The read count is normalized to the middle replicate to take into account that different sequencing libraries produce different numbers of sequences, such that the variation between the biological replicates reflects proportional differences in recombination frequency, and not absolute read count. An improvement of this method compared to Example 1 is that all V genes are detectable, because sonication is used. In Example 1, a small fraction of genes are not detectable because the restriction enzyme does not cut within or near the V gene. In FIG. 8, V genes in the locus that do not have reads are invariably V pseudogenes, that have a defect that precludes VDJ recombination, and thus they do not contribute to the repertoire.

Example 3

Oligonucleotide and RNA Hybridization

Example 3 may be performed in an analogous manner to Examples 1 and 2 except for the following:

Instead of using primer extension to deplete unrecombined segments of DNA and enrich for V(D)J recombined regions an alternative would be to preferentially deplete unrecombined regions and enrich for V(D)J recombined DNA using hybridisation, either with a set of strategically placed biotinylated oligonucleotides or biotinylated RNA, followed by separation using streptavidin magnetic beads.

(i) Oligonucleotide Hybridization

In the biotinylated oligonucleotides methodology a series of oligonucleotides similar in position to those used for depletion and enrichment in Examples 1 and 2 are hybridised to denatured genomic DNA and used to pull-down first unrecombined then second recombined DNA regions using streptavidin magnetic beads. Library production following these steps would be the same as for the other Examples described herein. If this step is only used to deplete unrecombined regions and is followed by the standard primer extension to isolate V(D)J recombined regions it would only be necessary to target the sense strand using antisense oligonucleotides since only the sense strand is a template for the primer extension using antisense oligonucleotides. Similarly, if this method was used for enrichment with J-specific oligonucleotides following depletion using intergenic antisense oligonucleotides it would only be necessary to use J-specific antisense oligonucleotides to target the sense strand of the already depleted DNA and hence enrich for V(D)J recombined DNA.

(ii) RNA Hybridization

In the biotinylated RNA methodology for depletion, regions just upstream of each J gene are amplified by PCR and cloned into a vector containing a T7 promoter sequence flanking the cloning site. These are then linearised at the opposite end of the insert to the T7 sequence and these are used as templates to produce biotinylated RNA using T7 polymerase. Large amounts of strand-specific biotinylated RNA can be made in this way as this enzyme is highly processive. This biotinylated RNA can then be used in a similar way to the oligonucleotides detailed above to hybridise to unrecombined regions in denatured genomic DNA and remove them using streptavidin magnetic beads. Depleting these regions would prevent them being targets for downstream primer extension reactions used to isolate V(D)J recombined DNA regions, as detailed in Examples 1 and 2. Again, if only used for the depletion step it would only be necessary to target the sense strand of the DNA using antisense RNA as the antisense strand of the DNA is not a template for the primer extension. This also means a larger region, and hence larger biotinylated RNA, can be used in the hybridisation step, which should aid hybridisation specificity and efficiency. RNA can easily be digested and removed from DNA following hybridisation.

For enrichment using the biotinylated RNA methodology, the J genes and regions just 3' (100-200 bp regions) could be cloned, linearised, used to produce biotinylated RNA and this then hybridised in a similar way to above but in this case to enrich for V(D)J recombined DNA. It would be best to do this after having already depleted for unrecombined regions. Again it would be best to use antisense RNA to target the sense strand in both depletion and enrichment steps as this would just leave unrecombined depleted, V(D)J enriched sense-strand DNA that would then be the perfect template for the standard PCR-based VDJ-seq library production as detailed in Examples 1 and 2, above.

Example 4

VDJ Recombination Product Identification Method Using RNA (A) Methods (i) Sample Material B cells are isolated from bone marrow or spleen from mice, or from human peripheral blood. RNA isolated by RNeasy or Trizol and DNase digested. Between 1-10 μg RNA is used per library preparation.

(ii) Reverse Transcription & RNA Degradation

1. Set up RT reaction based upon Superscript III (Invitrogen) protocol in 0.5 ml tube.

5 μl RNA 1-10 μg (up to 10 μl)
1 μl dNTPs (10 mM each)
1 μl primer mix* (2 μM)
6 μl water to 13 μl
Total: 13 μl volume

| Reverse Transcription primers | | |
|---|---|---|
| Primer | Sequence | SEQ ID NO |
| Human IgM RT | AAGGGTTGGGGCGGAT | 86 |
| Human IgG1-4 + IgE RT | GGGAAGACSGATGGGC | 87 |
| Human IgA1 & 2 RT | CAGCGGGAAGACCTTGG | 88 |
| Human IgD RT | CCTGATATGATGGGAACACA | 89 |

2. Incubate at 70° C. for 5 minutes, then 55° C. for 5 minutes.

3. Add the following mix, keeping the tube at 55° C.:

4 μl 5× FS buffer
1 μl DTT
1 μl RNasin
1 μl SSIII
Total: 20 μl volume

4. Mix, and incubate at 55° C. for 60 minutes, then 70° C. for 15 minutes.

5. Add 1 μl RNase H or A/T mix.

6. Incubate at 37° C. for 20 minutes.

7. Purify reaction using 1.0×SPRI beads and elute in 20 μl water.

(iii) Random Octamer to Add PE2 to 3' End cDNA

8. Set up 20 μl klenow exo-reaction in 0.5 ml tube (without klenow to start with). Use half reaction as a negative control without the oligo, or set up 2× reaction both with oligo.

10 μl cDNA
2 μl 10×NEB buffer 2
1 μl dNTPs (2 mM each, therefore 1:5 dilution of usual concentration)
1 μl random octamer+PE2 (100 μM)
5 μl water (to 19 μl)

| Random octamer + PE2 oligo | | |
|---|---|---|
| Primer | Sequence | SEQ ID NO |
| PE2 temp switch block 8N | GTGACTGGAGTTCAGACGTGTGCTCTTCCGATCTN NNNNNNN[SpcC3] | 90 | wherein [SpcC3] refers to a spacer with a 3' modification that prevents elongation.

9. Heat to 65° C. for 5 minutes (denature secondary structure) then 22° C. for 5 minutes (anneal octamers).

10. Add 1 μl Klenow exo-.

11. Incubate at 37° C. for 30 minutes, then 95° C. for 5 minutes to stop reaction and denature octamers from cDNA.

12. Transfer immediately to ice for 5 minutes.
13. Purify reaction using Qiagen QIAquick columns using PCR purification protocol or with 1.0×SPRI beads. Elute in 46 μl EB.

(iv) PCR to Generate Second Strand & Enrich VDJ Sequences

14. Perform PCR using Pwo master (Roche) with biotinylated constant region primers. Assemble reaction in PCR tubes. Each sample is divided into four separate 25 μl PCR reactions to increase library diversity. Include negative to control for PCR contamination by using 11.5 μl water instead of DNA.

| Mix 1 | | x5 |
|---|---|---|
| 12.5 μl Pwo master | | 62.5 μl |
| 0.5 μl F primer (10 μM Short PCR 2*) 4 μl | | 2.5 μl |
| 0.5 μl R primer mix (10 μM C PE1 Bio*) | | 2.5 μl |
| 11.5 μl DNA | | 46 μl |
| Total: 25 μl volume | | 125 μl |

Place on the PTC100 using the following conditions:
94° C. for 2 minutes, 12-15 cycles of: 94° C. for 15 seconds, 58° C. for 30 seconds, 72° C. for 45 seconds, followed by 72° C. for 5 minutes, and 4° C. pause. The final number of PCR cycles required may need titrating to achieve optimal amplification.

Primer sequences only include constant region primers of interest in the primer mix. These contain 8 random nucleotides to increase complexity at the start of the run. Short PE2 primer Tm: 61.87° C.; Constant-J primers Tm range: 61-63° C.

| Primer sequences to generate second strand & enrich VDJ sequences | | |
|---|---|---|
| Primer | Sequence | SEQ ID NO |
| Short PCR primer 2.0 | GTGACTGGAGTTCAGACGTGT | 91 |
| Constant region + PE1 IgM | ACACTCTTTCCCTACACGACGCTCTTCCGATCTNN NNNNNNCGGATGCACTCCCTGA | 92 |
| Constant region + PE1 IgG1 & 2 | ACACTCTTTCCCTACACGACGCTCTTCCGATCTNN NNNNNNCCTTGGTGGAGGCTGA | 93 |
| Constant region + PE1 IgD | ACACTCTTTCCCTACACGACGCTCTTCCGATCTCC TTGGTGGGTGCTGA | 94 |
| Constant region + PE1 IgA1 & 2 | ACACTCTTTCCCTACACGACGCTCTTCCGATCTNN NNNNNNGGTCGGGGATGCTGA | 95 |
| Constant region + PE1 IgE | ACACTCTTTCCCTACACGACGCTCTTCCGATCTGC TCTGTGTGGAGGCTGA | 96 |
| Constant region + PE1 IgG3 & 4 | ACACTCTTTCCCTACACGACGCTCTTCCGATCTCC TTGGTGGAAGCCTGA | 97 |

15. Pool the four separate PCR reactions into a single 1.5 ml tube. Purify using 0.8×SPRI beads to size select and remove primers/primer dimers. Elute in 46 μl water.

16. Prepare Dynabeads MyOne Streptavidin C1 beads (Invitrogen).

Vortex Dynabead stock, transfer 20 μl to eppendorf, add 1 ml 1× B&W+Tween buffer*, mix, place tube on magnet for 2 mins, discard supernatant. Resuspend beads in 20 μl of 1× B&W+Tween buffer, place on magnet and discard supernatant. Repeat 20 μl wash again. Resuspend beads in 20 μl of 1× B&W (no Tween) buffer, place on magnet and discard supernatant. Resuspend beads in 40 μl of 2× B&W (no Tween) buffer.

*2× B&W (Binding & Washing) buffer (with and without Tween-20)

| Final concentration | Stock | Amount for 50 ml |
|---|---|---|
| 10 mM Tris-HCl (pH 7.5) | 1M | 500 μl |
| 1 mM EDTA | 0.5M | 100 μl |
| 2M NaCl | 5M | 20 ml |
| 0.05% Tween-20100% | | 25 μl (Only include in Tween containing buffer) |
| Water | — | 29.4 ml |

17. Add 40 μl of DNA sample (step 15) to beads, mix and incubate for 60 mins, or overnight, on rotator at room temperature.

18. Place sample on magnet for 5 mins, discard supernatant. Wash beads twice in 100 μl 1× B&W (No Tween) buffer, and wash once in 100 μl EB (Qiagen). Resuspend beads in 50 μl buffer EB.

19. PCR using Expand Taq (Roche) with Short PCR 1 to Short PCR 2 primers. Assemble reaction in 200 μl tubes. Each sample is divided into 4 separate 50 μl PCR reactions to increase library diversity.

| | | x4 |
|---|---|---|
| Mix 1 | | |
| 1 μl dNTPs (10 mM each) | | 4 μl |
| 1 μl F primer (10 μM Short PCR 1*) | | 4 μl |
| 1 μl R primer (10 μM Short PCR 2*) | | 4 μl |
| 12.5 μl DNA | | 50 μl |
| 9.5 μl water | | 38 μl |
| 25 μl volume | | 100 μl |
| Mix 2 | | |
| 5 μl 10x PCR buffer | | 20 μl |
| 0.75 μl Expand Taq | | 3 μl |
| 19.25 μl water | | 77 μl |
| 25 μl volume | | 100 μl |

Aliquot 25 μl of Mix 1 into 4 separate PCR tubes on ice, add 25 μl Mix 2, mix, and quickly place on the Thermal cycler using the following conditions:
94° C. 2 mins, 5 cycles of: 94° C. 15 secs, 55° C. 30 secs, 72° C. 45 secs, followed by 72° C. 5 mins, and 4° C. pause.
*Primer sequences, Tms 61.8° C. and 58.2° C. respectively:

```
Short PCR primer 2.0
GTGACTGGAGTTCAGACGTGT     (SEQ ID NO: 91)

Short PCR primer 1.0
ACACTCTTTCCCTACACGAC      (SEQ ID NO: 98)
```

20. When PCR finished, combine 4 reactions into a single 1.5 ml tube. Place sample on magnet for 5 mins, pipette supernatant into clean eppendorf. Wash beads by resuspending in 30 μl EB buffer, place on magnet for 5 mins and transfer supernatant to the same tube as before. The tube containing the beads can be discarded (or resuspended in 50 μl EB and kept).

21. Purify reaction using Qiagen QIAquick columns using PCR purification protocol, elute in 40 μl buffer EB.

(v) Incorporation of Flowcell Binding & Barcoding Sequences by PCR

22. PCR using Pwo master (Roche) with universal Flowcell PE1 primer in combination with one of twelve index primers+PE2 per sample. Each sample is divided into four separate 25 μl PCR reactions to increase library diversity. Include negative control with 11.5 μl water instead of DNA.

| Mix | x5 |
| --- | --- |
| 12.5 μl Pwo master | 62.5 μl |
| 0.5 μl F primer (10 μM Flowcell PE1) | 2.5 μl |
| 0.5 μl R primer (10 μM Flowcell index PE2) | 2.5 μl |
| 11.5 μl DNA (1st round PCR) | 46 μl |
| Total: 25 μl volume | 125 μl |

Place on the PTC100 using the following conditions:

94° C. for 2 minutes, 7-9 cycles of: 94° C. for 15 seconds, 55° C. for 30 seconds, 72° C. for 45 seconds, followed by 72° C. for 5 minutes, and 4° C. pause. The final number of PCR cycles will require titration to achieve optimal amplification. Tms of regions annealing to target are 58.2° C. for PE1, and 61.9° C. for PE2.

| Flowcell Primer sequences | | |
| --- | --- | --- |
| Primer | Sequence | SEQ ID NO |
| Flowcell PE1 | AATGATACGGCGACCACCGAGATCTACACTCTTTCCC TACACGAC | 73 |
| Flowcell PE2 Index 1 | CAAGCAGAAGACGGCATACGAGATCGTGATGTGACT GGAGTTCAGACGTGT | 74 |
| Flowcell PE2 Index 2 | CAAGCAGAAGACGGCATACGAGATACATCGGTGACT GGAGTTCAGACGTGT | 75 |
| Flowcell PE2 Index 3 | CAAGCAGAAGACGGCATACGAGATGCCTAAGTGACT GGAGTTCAGACGTGT | 76 |
| Flowcell PE2 Index 4 | CAAGCAGAAGACGGCATACGAGATTGGTCAGTGACT GGAGTTCAGACGTGT | 77 |
| Flowcell PE2 Index 5 | CAAGCAGAAGACGGCATACGAGATCACTGTGTGACTG GAGTTCAGACGTGT | 78 |
| Flowcell PE2 Index 6 | CAAGCAGAAGACGGCATACGAGATATTGGCGTGACT GGAGTTCAGACGTGT | 79 |
| Flowcell PE2 Index 7 | CAAGCAGAAGACGGCATACGAGATGATCTGGTGACT GGAGTTCAGACGTGT | 80 |
| Flowcell PE2 Index 8 | CAAGCAGAAGACGGCATACGAGATTCAAGTGTGACTG AGTTCAGACGTGT | 81 |

See DNA protocol from Examples 1 and 2 for further index sequences.

23. Purify using 0.8×SPRI beads to size select and remove primers/primer dimers.

24. Determine concentration by picogreen or bioanalyser, perform QPCR checking for the presence of VDJ recombined products (e.g. V4-1 to JR) and absence of housekeeping genes (e.g. B2M).

The invention claimed is:

1. A method of identifying a VDJ recombination product which comprises the following steps:
    (a) obtaining a DNA sample comprising a VDJ recombination product;
    (b) fragmenting the VDJ recombination product by sonication, shearing or performing a restriction endonuclease reaction at a first site downstream of each of the J genes or downstream of the constant region, and a second site within or immediately upstream of the V gene to generate digested VDJ recombined fragments and unrecombined J fragments;
    (c) annealing oligonucleotides to the digested fragments at unique regions within or immediately downstream of each of the J genes;
    (d) separating the digested VDJ recombined fragments from the unrecombined J fragments and the rest of the genome;
    (e) sequencing the VDJ recombined fragments or products; and
    (f) data processing of the sequencing data to identify each VDJ recombination product and quantify VDJ recombination frequencies.

2. The method according to claim 1, wherein the DNA sample comprising a VDJ recombination product comprises a cell population.

3. The method according to claim 2, wherein the cell population is obtained from a human or a mouse.

4. The method according to claim 2, wherein the cell population comprises an immunoglobulin containing cell.

5. The method according to claim 1, wherein the DNA sample comprising a VDJ recombination product comprises a library of VDJ recombined DNA samples obtained from an in vitro antibody production system.

6. The method according to claim 1, wherein the VDJ recombination product is derived from a heavy chain immunoglobulin.

7. The method according to claim 1, wherein the VDJ recombination product is derived from a light chain immunoglobulin.

8. The method according to claim 1, wherein the VDJ recombination product is derived from a T cell receptor.

9. The method according to claim 2, wherein the cell population comprises mouse cells and the oligonucleotides are selected from the group consisting of SEQ ID NOS: 1 to 4 and 47 to 50.

10. The method according to claim 2, wherein the cell population comprises human cells and the oligonucleotides are selected from the group consisting of SEQ ID NOS: 51 to 56.

11. The method according to claim 1, wherein the DNA sample is fragmented by sonication.

12. The method according to claim 1, wherein the DNA sample is fragmented by performing a restriction endonuclease reaction.

13. The method according to claim 12, wherein the restriction endonuclease enzyme used in step (b) is selected from DpnII and/or NlaIII.

14. The method according to claim 12, wherein step (b) comprises the use of a further restriction endonuclease enzyme, wherein the further restriction endonuclease enzyme is an enzyme which is specific for a region upstream of the V gene.

15. The method according to claim 1, wherein step (c) additionally comprises the step of performing primer extension, oligonucleotide hybridization and/or reverse transcription.

16. The method according to claim 1, wherein step (c) comprises tagging the digested fragments with one member of a binding pair.

17. The method according to claim 1, which additionally comprises the addition of a first adapter molecule to one end of the VDJ recombination product following step (c).

18. The method according to claim 17, wherein the restriction endonuclease used in step (b) is NlaIII and the adapter molecule has the sequence of SEQ ID NO: 5.

19. The method according to claim 17, wherein the restriction endonuclease used in step (b) is DpnII and the adapter molecule has the sequence of SEQ ID NO: 6.

20. The method according to claim 17, further comprising addition of a second adapter molecule to a second end of the VDJ recombination product.

21. The method according to claim 20, wherein the cell population comprises mouse cells and the oligonucleotides for the addition of the second adaptor are selected from the group consisting of SEQ ID NOS: 7 to 11 and 57 to 65.

22. The method according to claim 20, wherein the cell population comprises human cells and the oligonucleotides for the addition of the second adaptor are selected from the group consisting of SEQ ID NOS: 66 to 72.

23. The method according to claim 1, wherein step (d) comprises the use of oligonucleotides specific to the upstream region of each of the J genes on both strands.

24. The method according to claim 23, wherein the cell population comprises mouse cells and the oligonucleotides used in step (d) are selected from the group consisting of SEQ ID NOS: 12 to 19 and 24 to 34.

25. The method according to claim 23, wherein the cell population comprises human cells and the oligonucleotides used in step (d) are selected from the group consisting of SEQ ID NOS: 39 to 46.

26. The method according to claim 4, wherein the immunoglobulin containing cell is a T cell or a B cell.

27. The method according to claim 16, wherein the binding pair is biotin and streptavidin or an antigen and an antibody.

* * * * *

SEQUENCE LISTING

<160> NUMBER OF SEQ ID NOS: 98

<210> SEQ ID NO 1
<211> LENGTH: 21
<212> TYPE: DNA
<213> ORGANISM: Artificial
<220> FEATURE:
<223> OTHER INFORMATION: Synthetic Oligonucleotide

<400> SEQUENCE: 1
agccagctta cctgaggaga c                    21

<210> SEQ ID NO 2
<211> LENGTH: 23
<212> TYPE: DNA
<213> ORGANISM: Artificial
<220> FEATURE:
<223> OTHER INFORMATION: Synthetic Oligonucleotide

<400> SEQUENCE: 2

-continued gagaggttgt aaggactcac ctg                                              23

<210> SEQ ID NO 3
<211> LENGTH: 23
<212> TYPE: DNA
<213> ORGANISM: Artificial
<220> FEATURE:
<223> OTHER INFORMATION: Synthetic Oligonucleotide

<400> SEQUENCE: 3
agttaggact cacctgcaga gac                                              23

<210> SEQ ID NO 4
<211> LENGTH: 21
<212> TYPE: DNA
<213> ORGANISM: Artificial
<220> FEATURE:
<223> OTHER INFORMATION: Synthetic Oligonucleotide

<400> SEQUENCE: 4
aggccattct tacctgagga g                                                21

<210> SEQ ID NO 5
<211> LENGTH: 70
<212> TYPE: DNA
<213> ORGANISM: Artificial
<220> FEATURE:
<223> OTHER INFORMATION: Synthetic Primer

<400> SEQUENCE: 5
acactctttc cctacacgac gctcttccga tctcatgtgt gagaaaggga tgtgctgcga      60
gaaggctaga                                                             70

<210> SEQ ID NO 6
<211> LENGTH: 70
<212> TYPE: DNA
<213> ORGANISM: Artificial
<220> FEATURE:
<223> OTHER INFORMATION: Synthetic Primer

<400> SEQUENCE: 6
acactctttc cctacacgac gctcttccga tcttgtgaga aagggatgtg ctgcgagaag      60
gctagactag                                                             70

<210> SEQ ID NO 7
<211> LENGTH: 33
<212> TYPE: DNA
<213> ORGANISM: Artificial
<220> FEATURE:
<223> OTHER INFORMATION: Synthetic Primer

<400> SEQUENCE: 7
acactctttc cctacacgac gctcttccga tct                                   33

<210> SEQ ID NO 8
<211> LENGTH: 53
<212> TYPE: DNA
<213> ORGANISM: Artificial
<220> FEATURE:
<223> OTHER INFORMATION: Synthetic Primer

<400> SEQUENCE: 8
ctcggcattc ctgctgaacc gctcttccga tctcccagac atcgaagtac cag             53

```
<210> SEQ ID NO 9
<211> LENGTH: 52
<212> TYPE: DNA
<213> ORGANISM: Artificial
<220> FEATURE:
<223> OTHER INFORMATION: Synthetic Primer

<400> SEQUENCE: 9
ctcggcattc ctgctgaacc gctcttccga tctttggccc cagtagtcaa ag          52

<210> SEQ ID NO 10
<211> LENGTH: 51
<212> TYPE: DNA
<213> ORGANISM: Artificial
<220> FEATURE:
<223> OTHER INFORMATION: Synthetic Primer

<400> SEQUENCE: 10
ctcggcattc ctgctgaacc gctcttccga tcttggcccc agtaagcaaa c           51

<210> SEQ ID NO 11
<211> LENGTH: 54
<212> TYPE: DNA
<213> ORGANISM: Artificial
<220> FEATURE:
<223> OTHER INFORMATION: Synthetic Primer

<400> SEQUENCE: 11
ctcggcattc ctgctgaacc gctcttccga tctccccagt agtccatagc atag        54

<210> SEQ ID NO 12
<211> LENGTH: 20
<212> TYPE: DNA
<213> ORGANISM: Artificial
<220> FEATURE:
<223> OTHER INFORMATION: Synthetic Oligonucleotide

<400> SEQUENCE: 12
atctgagttt ctgaggcttg                                              20

<210> SEQ ID NO 13
<211> LENGTH: 20
<212> TYPE: DNA
<213> ORGANISM: Artificial
<220> FEATURE:
<223> OTHER INFORMATION: Synthetic Oligonucleotide

<400> SEQUENCE: 13
aaaactctct ccacatcctg                                              20

<210> SEQ ID NO 14
<211> LENGTH: 23
<212> TYPE: DNA
<213> ORGANISM: Artificial
<220> FEATURE:
<223> OTHER INFORMATION: Synthetic Oligonucleotide

<400> SEQUENCE: 14
ctaaaggggt ctatgatagt gtg                                          23

<210> SEQ ID NO 15
<211> LENGTH: 21
<212> TYPE: DNA
<213> ORGANISM: Artificial
<220> FEATURE:
<223> OTHER INFORMATION: Synthetic Oligonucleotide
```

```
<400> SEQUENCE: 15
gtgtacaaaa acccatctac c                                      21

<210> SEQ ID NO 16
<211> LENGTH: 19
<212> TYPE: DNA
<213> ORGANISM: Artificial
<220> FEATURE:
<223> OTHER INFORMATION: Synthetic Oligonucleotide

<400> SEQUENCE: 16
cattgttgtc acaatgtgc                                         19

<210> SEQ ID NO 17
<211> LENGTH: 21
<212> TYPE: DNA
<213> ORGANISM: Artificial
<220> FEATURE:
<223> OTHER INFORMATION: Synthetic Oligonucleotide

<400> SEQUENCE: 17
ttagacccct gacaataaat g                                      21

<210> SEQ ID NO 18
<211> LENGTH: 20
<212> TYPE: DNA
<213> ORGANISM: Artificial
<220> FEATURE:
<223> OTHER INFORMATION: Synthetic Oligonucleotide

<400> SEQUENCE: 18
gtggaacaat gacttgaatg                                        20

<210> SEQ ID NO 19
<211> LENGTH: 19
<212> TYPE: DNA
<213> ORGANISM: Artificial
<220> FEATURE:
<223> OTHER INFORMATION: Synthetic Oligonucleotide

<400> SEQUENCE: 19
tgggcaactc agacattat                                         19

<210> SEQ ID NO 20
<211> LENGTH: 58
<212> TYPE: DNA
<213> ORGANISM: Artificial
<220> FEATURE:
<223> OTHER INFORMATION: Synthetic Primer

<400> SEQUENCE: 20
aatgatacgg cgaccaccga gatctacact ctttccctac acgacgctct tccgatct    58

<210> SEQ ID NO 21
<211> LENGTH: 61
<212> TYPE: DNA
<213> ORGANISM: Artificial
<220> FEATURE:
<223> OTHER INFORMATION: Synthetic Primer

<400> SEQUENCE: 21
caagcagaag acggcatacg agatcggtct cggcattcct gctgaaccgc tcttccgatc    60
t                                                             61
```

```
<210> SEQ ID NO 22
<211> LENGTH: 33
<212> TYPE: DNA
<213> ORGANISM: Artificial
<220> FEATURE:
<223> OTHER INFORMATION: Synthetic Primer

<400> SEQUENCE: 22
acactctttc cctacacgac gctcttccga tct                           33

<210> SEQ ID NO 23
<211> LENGTH: 12
<212> TYPE: DNA
<213> ORGANISM: Artificial
<220> FEATURE:
<223> OTHER INFORMATION: Synthetic Primer

<400> SEQUENCE: 23
cgagaaggct ag                                                  12

<210> SEQ ID NO 24
<211> LENGTH: 20
<212> TYPE: DNA
<213> ORGANISM: Artificial
<220> FEATURE:
<223> OTHER INFORMATION: Synthetic Primer

<400> SEQUENCE: 24
acagaggcag aacagagact                                          20

<210> SEQ ID NO 25
<211> LENGTH: 22
<212> TYPE: DNA
<213> ORGANISM: Artificial
<220> FEATURE:
<223> OTHER INFORMATION: Synthetic Primer

<400> SEQUENCE: 25
agaggaaaaa tccactattg tg                                       22

<210> SEQ ID NO 26
<211> LENGTH: 22
<212> TYPE: DNA
<213> ORGANISM: Artificial
<220> FEATURE:
<223> OTHER INFORMATION: Synthetic Primer

<400> SEQUENCE: 26
ccagagtctg actagaatca cc                                       22

<210> SEQ ID NO 27
<211> LENGTH: 21
<212> TYPE: DNA
<213> ORGANISM: Artificial
<220> FEATURE:
<223> OTHER INFORMATION: Synthetic Primer

<400> SEQUENCE: 27
tacagccaga cagtggagta c                                        21

<210> SEQ ID NO 28
<211> LENGTH: 20
<212> TYPE: DNA
<213> ORGANISM: Artificial
<220> FEATURE:
<223> OTHER INFORMATION: Synthetic Primer
```

<400> SEQUENCE: 28
cctcactgaa gaggaacaga                                          20

<210> SEQ ID NO 29
<211> LENGTH: 18
<212> TYPE: DNA
<213> ORGANISM: Artificial
<220> FEATURE:
<223> OTHER INFORMATION: Synthetic Primer

<400> SEQUENCE: 29
ttgagtgaag ggacacca                                            18

<210> SEQ ID NO 30
<211> LENGTH: 20
<212> TYPE: DNA
<213> ORGANISM: Artificial
<220> FEATURE:
<223> OTHER INFORMATION: Synthetic Primer

<400> SEQUENCE: 30
cccatacaaa aactgagcat                                          20

<210> SEQ ID NO 31
<211> LENGTH: 23
<212> TYPE: DNA
<213> ORGANISM: Artificial
<220> FEATURE:
<223> OTHER INFORMATION: Synthetic Primer

<400> SEQUENCE: 31
ctgaacttag cctatctaac tgg                                      23

<210> SEQ ID NO 32
<211> LENGTH: 20
<212> TYPE: DNA
<213> ORGANISM: Artificial
<220> FEATURE:
<223> OTHER INFORMATION: Synthetic Primer

<400> SEQUENCE: 32
tttacaaaaa cctgcctgag                                          20

<210> SEQ ID NO 33
<211> LENGTH: 21
<212> TYPE: DNA
<213> ORGANISM: Artificial
<220> FEATURE:
<223> OTHER INFORMATION: Synthetic Primer

<400> SEQUENCE: 33
gcatgtcata gtcctcactg t                                        21

<210> SEQ ID NO 34
<211> LENGTH: 20
<212> TYPE: DNA
<213> ORGANISM: Artificial
<220> FEATURE:
<223> OTHER INFORMATION: Synthetic Primer

<400> SEQUENCE: 34
tctctacaaa aacctgcctg                                          20

<210> SEQ ID NO 35
<211> LENGTH: 18

<210> SEQ ID NO 35
<211> LENGTH: 18
<212> TYPE: DNA
<213> ORGANISM: Artificial
<220> FEATURE:
<223> OTHER INFORMATION: Synthetic Primer

<400> SEQUENCE: 35
cagggctgac tcaccgtg                                                 18

<210> SEQ ID NO 36
<211> LENGTH: 17
<212> TYPE: DNA
<213> ORGANISM: Artificial
<220> FEATURE:
<223> OTHER INFORMATION: Synthetic Primer

<400> SEQUENCE: 36
cagaaaccca cagcccg                                                  17

<210> SEQ ID NO 37
<211> LENGTH: 23
<212> TYPE: DNA
<213> ORGANISM: Artificial
<220> FEATURE:
<223> OTHER INFORMATION: Synthetic Primer

<400> SEQUENCE: 37 gtgttttgt atgggagaag cag                                            23

<210> SEQ ID NO 38
<211> LENGTH: 18
<212> TYPE: DNA
<213> ORGANISM: Artificial
<220> FEATURE:
<223> OTHER INFORMATION: Synthetic Primer

<400> SEQUENCE: 38
cacagcctct gccctcct                                                 18

<210> SEQ ID NO 39
<211> LENGTH: 19
<212> TYPE: DNA
<213> ORGANISM: Artificial
<220> FEATURE:
<223> OTHER INFORMATION: Synthetic Primer

<400> SEQUENCE: 39
acgggcacag gtttgtgtc                                                19

<210> SEQ ID NO 40
<211> LENGTH: 18
<212> TYPE: DNA
<213> ORGANISM: Artificial
<220> FEATURE:
<223> OTHER INFORMATION: Synthetic Primer

<400> SEQUENCE: 40
gtccctgttc ctgcccag                                                 18

<210> SEQ ID NO 41
<211> LENGTH: 22
<212> TYPE: DNA
<213> ORGANISM: Artificial
<220> FEATURE:
<223> OTHER INFORMATION: Synthetic Primer

<400> SEQUENCE: 41
gtcggagagt caggttttg tg                                    22

<210> SEQ ID NO 42
<211> LENGTH: 19
<212> TYPE: DNA
<213> ORGANISM: Artificial
<220> FEATURE:
<223> OTHER INFORMATION: Synthetic Primer

<400> SEQUENCE: 42
agtcacattg tgggaggcc                                       19

<210> SEQ ID NO 43
<211> LENGTH: 19
<212> TYPE: DNA
<213> ORGANISM: Artificial
<220> FEATURE:
<223> OTHER INFORMATION: Synthetic Primer

<400> SEQUENCE: 43
gtctgagagg gtcccaggg                                       19

<210> SEQ ID NO 44
<211> LENGTH: 20
<212> TYPE: DNA
<213> ORGANISM: Artificial
<220> FEATURE:
<223> OTHER INFORMATION: Synthetic Primer

<400> SEQUENCE: 44
gtgacaacaa tgccaggacc                                      20

<210> SEQ ID NO 45
<211> LENGTH: 20
<212> TYPE: DNA
<213> ORGANISM: Artificial
<220> FEATURE:
<223> OTHER INFORMATION: Synthetic Primer

<400> SEQUENCE: 45
ggtgaggatg gacattctgc                                      20

<210> SEQ ID NO 46
<211> LENGTH: 19
<212> TYPE: DNA
<213> ORGANISM: Artificial
<220> FEATURE:
<223> OTHER INFORMATION: Synthetic Primer

<400> SEQUENCE: 46
cagccaccca gagaccttc                                       19

<210> SEQ ID NO 47
<211> LENGTH: 26
<212> TYPE: DNA
<213> ORGANISM: Artificial
<220> FEATURE:
<223> OTHER INFORMATION: Synthetic Primer

<400> SEQUENCE: 47
gaaagagact ttggattcta cttacg                               26

<210> SEQ ID NO 48
<211> LENGTH: 27
<212> TYPE: DNA
<213> ORGANISM: Artificial

```
<220> FEATURE:
<223> OTHER INFORMATION: Synthetic Primer

<400> SEQUENCE: 48
gaacaagagt tgagaagact acttacg                                             27

<210> SEQ ID NO 49
<211> LENGTH: 27
<212> TYPE: DNA
<213> ORGANISM: Artificial
<220> FEATURE:
<223> OTHER INFORMATION: Synthetic Primer

<400> SEQUENCE: 49
cacaagtaaa tgagcaaaag tctactt                                             27

<210> SEQ ID NO 50
<211> LENGTH: 28
<212> TYPE: DNA
<213> ORGANISM: Artificial
<220> FEATURE:
<223> OTHER INFORMATION: Synthetic Primer

<400> SEQUENCE: 50
aaagatgaga aaagtgtact tacgtttc                                            28

<210> SEQ ID NO 51
<211> LENGTH: 20
<212> TYPE: DNA
<213> ORGANISM: Artificial
<220> FEATURE:
<223> OTHER INFORMATION: Synthetic Primer

<400> SEQUENCE: 51
ccagacagca gactcacctg                                                     20

<210> SEQ ID NO 52
<211> LENGTH: 18
<212> TYPE: DNA
<213> ORGANISM: Artificial
<220> FEATURE:
<223> OTHER INFORMATION: Synthetic Primer

<400> SEQUENCE: 52
tgcagtggga ctcacctg                                                       18

<210> SEQ ID NO 53
<211> LENGTH: 22
<212> TYPE: DNA
<213> ORGANISM: Artificial
<220> FEATURE:
<223> OTHER INFORMATION: Synthetic Primer

<400> SEQUENCE: 53
agaaggaaag ccatcttacc tg                                                  22

<210> SEQ ID NO 54
<211> LENGTH: 22
<212> TYPE: DNA
<213> ORGANISM: Artificial
<220> FEATURE:
<223> OTHER INFORMATION: Synthetic Primer

<400> SEQUENCE: 54
caggagagag gttgtgagga ct                                                  22
```

-continued

<210> SEQ ID NO 55
<211> LENGTH: 18
<212> TYPE: DNA
<213> ORGANISM: Artificial
<220> FEATURE:
<223> OTHER INFORMATION: Synthetic Primer

<400> SEQUENCE: 55 aggggtggt gaggactc                                                    18

<210> SEQ ID NO 56
<211> LENGTH: 21
<212> TYPE: DNA
<213> ORGANISM: Artificial
<220> FEATURE:
<223> OTHER INFORMATION: Synthetic Primer

<400> SEQUENCE: 56
ccattcttac ctgaggagac g                                               21

<210> SEQ ID NO 57
<211> LENGTH: 25
<212> TYPE: DNA
<213> ORGANISM: Artificial
<220> FEATURE:
<223> OTHER INFORMATION: Synthetic Primer

<400> SEQUENCE: 57
acactctttc cctacacgac gctct                                           25

<210> SEQ ID NO 58
<211> LENGTH: 55
<212> TYPE: DNA
<213> ORGANISM: Artificial
<220> FEATURE:
<223> OTHER INFORMATION: Synthetic Primer

<400> SEQUENCE: 58
gtgactggag ttcagacgtg tgctcttccg atctccctgt gccccagaca tcgaa          55

<210> SEQ ID NO 59
<211> LENGTH: 56
<212> TYPE: DNA
<213> ORGANISM: Artificial
<220> FEATURE:
<223> OTHER INFORMATION: Synthetic Primer

<400> SEQUENCE: 59
gtgactggag ttcagacgtg tgctcttccg atctagtggt gccttggccc cagtag         56

<210> SEQ ID NO 60
<211> LENGTH: 58
<212> TYPE: DNA
<213> ORGANISM: Artificial
<220> FEATURE:
<223> OTHER INFORMATION: Synthetic Primer

<400> SEQUENCE: 60
gtgactggag ttcagacgtg tgctcttccg atctaccaga gtcccttggc cccagtaa       58

<210> SEQ ID NO 61
<211> LENGTH: 62
<212> TYPE: DNA
<213> ORGANISM: Artificial
<220> FEATURE:
<223> OTHER INFORMATION: Synthetic Primer -continued

<400> SEQUENCE: 61
gtgactggag ttcagacgtg tgctcttccg atcttgaggt tccttgaccc cagtagtcca    60
ta                                                                  62

<210> SEQ ID NO 62
<211> LENGTH: 58
<212> TYPE: DNA
<213> ORGANISM: Artificial
<220> FEATURE:
<223> OTHER INFORMATION: Synthetic Primer

<400> SEQUENCE: 62
gtgactggag ttcagacgtg tgctcttccg atcttttgat ttccagcttg gtgcctcc     58

<210> SEQ ID NO 63
<211> LENGTH: 58
<212> TYPE: DNA
<213> ORGANISM: Artificial
<220> FEATURE:
<223> OTHER INFORMATION: Synthetic Primer

<400> SEQUENCE: 63
gtgactggag ttcagacgtg tgctcttccg atctttttatt tccagcttgg tccccccct    58

<210> SEQ ID NO 64
<211> LENGTH: 60
<212> TYPE: DNA
<213> ORGANISM: Artificial
<220> FEATURE:
<223> OTHER INFORMATION: Synthetic Primer

<400> SEQUENCE: 64
gtgactggag ttcagacgtg tgctcttccg atctcgtttt atttccaact ttgtccccga    60

<210> SEQ ID NO 65
<211> LENGTH: 55
<212> TYPE: DNA
<213> ORGANISM: Artificial
<220> FEATURE:
<223> OTHER INFORMATION: Synthetic Primer

<400> SEQUENCE: 65
gtgactggag ttcagacgtg tgctcttccg atctcagctc cagcttggtc ccagc         55

<210> SEQ ID NO 66
<211> LENGTH: 52
<212> TYPE: DNA
<213> ORGANISM: Artificial
<220> FEATURE:
<223> OTHER INFORMATION: Synthetic Primer

<400> SEQUENCE: 66
gtgactggag ttcagacgtg tgctcttccg atctggtgcc ctggccccag tg            52

<210> SEQ ID NO 67
<211> LENGTH: 53
<212> TYPE: DNA
<213> ORGANISM: Artificial
<220> FEATURE:
<223> OTHER INFORMATION: Synthetic Primer

<400> SEQUENCE: 67
gtgactggag ttcagacgtg tgctcttccg atctggtgcc acggccccag aga           53

<210> SEQ ID NO 68
<211> LENGTH: 55
<212> TYPE: DNA
<213> ORGANISM: Artificial
<220> FEATURE:
<223> OTHER INFORMATION: Synthetic Primer

<400> SEQUENCE: 68
gtgactggag ttcagacgtg tgctcttccg atctaccatt gtcccttggc cccag       55

<210> SEQ ID NO 69
<211> LENGTH: 54
<212> TYPE: DNA
<213> ORGANISM: Artificial
<220> FEATURE:
<223> OTHER INFORMATION: Synthetic Primer

<400> SEQUENCE: 69
gtgactggag ttcagacgtg tgctcttccg atctgaccag ggtyccytgg cccc        54

<210> SEQ ID NO 70
<211> LENGTH: 54
<212> TYPE: DNA
<213> ORGANISM: Artificial
<220> FEATURE:
<223> OTHER INFORMATION: Synthetic Primer

<400> SEQUENCE: 70
gtgactggag ttcagacgtg tgctcttccg atctcagggt tccytggccc cagg        54

<210> SEQ ID NO 71
<211> LENGTH: 59
<212> TYPE: DNA
<213> ORGANISM: Artificial
<220> FEATURE:
<223> OTHER INFORMATION: Synthetic Primer

<400> SEQUENCE: 71
gtgactggag ttcagacgtg tgctcttccg atctcctttg ccccagacgt ccatgtagt    59

<210> SEQ ID NO 72
<211> LENGTH: 56
<212> TYPE: DNA
<213> ORGANISM: Artificial
<220> FEATURE:
<223> OTHER INFORMATION: Synthetic Primer

<400> SEQUENCE: 72
gtgactggag ttcagacgtg tgctcttccg atcttksccc cagacgtcca taccgt      56

<210> SEQ ID NO 73
<211> LENGTH: 45
<212> TYPE: DNA
<213> ORGANISM: Artificial
<220> FEATURE:
<223> OTHER INFORMATION: Synthetic Primer

<400> SEQUENCE: 73
aatgatacgg cgaccaccga gatctacact ctttccctac acgac                  45

<210> SEQ ID NO 74
<211> LENGTH: 51
<212> TYPE: DNA
<213> ORGANISM: Artificial
<220> FEATURE:
<223> OTHER INFORMATION: Synthetic Primer -continued

<400> SEQUENCE: 74
caagcagaag acggcatacg agatcgtgat gtgactggag ttcagacgtg t    51

<210> SEQ ID NO 75
<211> LENGTH: 51
<212> TYPE: DNA
<213> ORGANISM: Artificial
<220> FEATURE:
<223> OTHER INFORMATION: Synthetic Primer

<400> SEQUENCE: 75
caagcagaag acggcatacg agatacatcg gtgactggag ttcagacgtg t    51

<210> SEQ ID NO 76
<211> LENGTH: 51
<212> TYPE: DNA
<213> ORGANISM: Artificial
<220> FEATURE:
<223> OTHER INFORMATION: Synthetic Primer

<400> SEQUENCE: 76
caagcagaag acggcatacg agatgcctaa gtgactggag ttcagacgtg t    51

<210> SEQ ID NO 77
<211> LENGTH: 51
<212> TYPE: DNA
<213> ORGANISM: Artificial
<220> FEATURE:
<223> OTHER INFORMATION: Synthetic Primer

<400> SEQUENCE: 77
caagcagaag acggcatacg agattggtca gtgactggag ttcagacgtg t    51

<210> SEQ ID NO 78
<211> LENGTH: 51
<212> TYPE: DNA
<213> ORGANISM: Artificial
<220> FEATURE:
<223> OTHER INFORMATION: Synthetic Primer

<400> SEQUENCE: 78
caagcagaag acggcatacg agatcactgt gtgactggag ttcagacgtg t    51

<210> SEQ ID NO 79
<211> LENGTH: 51
<212> TYPE: DNA
<213> ORGANISM: Artificial
<220> FEATURE:
<223> OTHER INFORMATION: Synthetic Primer

<400> SEQUENCE: 79
caagcagaag acggcatacg agatattggc gtgactggag ttcagacgtg t    51

<210> SEQ ID NO 80
<211> LENGTH: 51
<212> TYPE: DNA
<213> ORGANISM: Artificial
<220> FEATURE:
<223> OTHER INFORMATION: Synthetic Primer

<400> SEQUENCE: 80
caagcagaag acggcatacg agatgatctg gtgactggag ttcagacgtg t    51

<210> SEQ ID NO 81

<210> SEQ ID NO 81
<211> LENGTH: 51
<212> TYPE: DNA
<213> ORGANISM: Artificial
<220> FEATURE:
<223> OTHER INFORMATION: Synthetic Primer

<400> SEQUENCE: 81
caagcagaag acggcatacg agattcaagt gtgactggag ttcagacgtg t          51

<210> SEQ ID NO 82
<211> LENGTH: 51
<212> TYPE: DNA
<213> ORGANISM: Artificial
<220> FEATURE:
<223> OTHER INFORMATION: Synthetic Primer

<400> SEQUENCE: 82
caagcagaag acggcatacg agatctgatc gtgactggag ttcagacgtg t          51

<210> SEQ ID NO 83
<211> LENGTH: 51
<212> TYPE: DNA
<213> ORGANISM: Artificial
<220> FEATURE:
<223> OTHER INFORMATION: Synthetic Primer

<400> SEQUENCE: 83
caagcagaag acggcatacg agataagcta gtgactggag ttcagacgtg t          51

<210> SEQ ID NO 84
<211> LENGTH: 51
<212> TYPE: DNA
<213> ORGANISM: Artificial
<220> FEATURE:
<223> OTHER INFORMATION: Synthetic Primer

<400> SEQUENCE: 84
caagcagaag acggcatacg agatgtagcc gtgactggag ttcagacgtg t          51

<210> SEQ ID NO 85
<211> LENGTH: 51
<212> TYPE: DNA
<213> ORGANISM: Artificial
<220> FEATURE:
<223> OTHER INFORMATION: Synthetic Primer

<400> SEQUENCE: 85
caagcagaag acggcatacg agattacaag gtgactggag ttcagacgtg t          51

<210> SEQ ID NO 86
<211> LENGTH: 16
<212> TYPE: DNA
<213> ORGANISM: Artificial
<220> FEATURE:
<223> OTHER INFORMATION: Synthetic Primer

<400> SEQUENCE: 86
aagggttggg gcggat                                                 16

<210> SEQ ID NO 87
<211> LENGTH: 16
<212> TYPE: DNA
<213> ORGANISM: Artificial
<220> FEATURE:
<223> OTHER INFORMATION: Synthetic Primer

<400> SEQUENCE: 87

-continued gggaagacsg atgggc                                              16

<210> SEQ ID NO 88
<211> LENGTH: 17
<212> TYPE: DNA
<213> ORGANISM: Artificial
<220> FEATURE:
<223> OTHER INFORMATION: Synthetic Primer

<400> SEQUENCE: 88
cagcgggaag accttgg                                             17

<210> SEQ ID NO 89
<211> LENGTH: 21
<212> TYPE: DNA
<213> ORGANISM: Artificial
<220> FEATURE:
<223> OTHER INFORMATION: Synthetic Primer

<400> SEQUENCE: 89
cctgatatga tgggaacac a                                         21

<210> SEQ ID NO 90
<211> LENGTH: 42
<212> TYPE: DNA
<213> ORGANISM: Artificial
<220> FEATURE:
<223> OTHER INFORMATION: Synthetic Primer
<220> FEATURE:
<221> NAME/KEY: misc_feature
<222> LOCATION: (35)..(42)
<223> OTHER INFORMATION: n is a, c, g, or t

<400> SEQUENCE: 90
gtgactggag ttcagacgtg tgctcttccg atctnnnnnn nn                  42

<210> SEQ ID NO 91
<211> LENGTH: 21
<212> TYPE: DNA
<213> ORGANISM: Artificial
<220> FEATURE:
<223> OTHER INFORMATION: Synthetic Primer

<400> SEQUENCE: 91
gtgactggag ttcagacgtg t                                        21

<210> SEQ ID NO 92
<211> LENGTH: 57
<212> TYPE: DNA
<213> ORGANISM: Artificial
<220> FEATURE:
<223> OTHER INFORMATION: Synthetic Primer
<220> FEATURE:
<221> NAME/KEY: misc_feature
<222> LOCATION: (34)..(41)
<223> OTHER INFORMATION: n is a, c, g, or t

<400> SEQUENCE: 92
acactctttc cctacacgac gctcttccga tctnnnnnnn ncggatgcac tccctga   57

<210> SEQ ID NO 93
<211> LENGTH: 57
<212> TYPE: DNA
<213> ORGANISM: Artificial
<220> FEATURE:
<223> OTHER INFORMATION: Synthetic Primer
<220> FEATURE:

```
<221> NAME/KEY: misc_feature
<222> LOCATION: (34)..(41)
<223> OTHER INFORMATION: n is a, c, g, or t

<400> SEQUENCE: 93
acactctttc cctacacgac gctcttccga tctnnnnnnn nccttggtgg aggctga      57

<210> SEQ ID NO 94
<211> LENGTH: 49
<212> TYPE: DNA
<213> ORGANISM: Artificial
<220> FEATURE:
<223> OTHER INFORMATION: Synthetic Primer

<400> SEQUENCE: 94
acactctttc cctacacgac gctcttccga tctccttggt gggtgctga               49

<210> SEQ ID NO 95
<211> LENGTH: 56
<212> TYPE: DNA
<213> ORGANISM: Artificial
<220> FEATURE:
<223> OTHER INFORMATION: Synthetic Primer
<220> FEATURE:
<221> NAME/KEY: misc_feature
<222> LOCATION: (34)..(41)
<223> OTHER INFORMATION: n is a, c, g, or t

<400> SEQUENCE: 95
acactctttc cctacacgac gctcttccga tctnnnnnnn nggtcgggga tgctga       56

<210> SEQ ID NO 96
<211> LENGTH: 51
<212> TYPE: DNA
<213> ORGANISM: Artificial
<220> FEATURE:
<223> OTHER INFORMATION: Synthetic Primer

<400> SEQUENCE: 96
acactctttc cctacacgac gctcttccga tctgctctgt gtggaggctg a            51

<210> SEQ ID NO 97
<211> LENGTH: 50
<212> TYPE: DNA
<213> ORGANISM: Artificial
<220> FEATURE:
<223> OTHER INFORMATION: Synthetic Primer

<400> SEQUENCE: 97
acactctttc cctacacgac gctcttccga tctccttggt ggaagcctga              50

<210> SEQ ID NO 98
<211> LENGTH: 20
<212> TYPE: DNA
<213> ORGANISM: Artificial
<220> FEATURE:
<223> OTHER INFORMATION: Synthetic Primer

<400> SEQUENCE: 98
acactctttc cctacacgac                                               20
```